(12) United States Patent
Harttig

(10) Patent No.: US 11,510,601 B2
(45) Date of Patent: Nov. 29, 2022

(54) SENSOR AND SENSOR ASSEMBLY FOR DETECTING AN ANALYTE IN A BODY FLUID

(71) Applicant: Roche Diabetes Care, Inc., Indianapolis, IN (US)

(72) Inventor: Herbert Harttig, Neustadt (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 657 days.

(21) Appl. No.: 15/767,471

(22) PCT Filed: Nov. 18, 2016

(86) PCT No.: PCT/EP2016/078179
§ 371 (c)(1),
(2) Date: Apr. 11, 2018

(87) PCT Pub. No.: WO2017/085280
PCT Pub. Date: May 26, 2017

(65) Prior Publication Data
US 2018/0296146 A1 Oct. 18, 2018

(30) Foreign Application Priority Data
Nov. 19, 2015 (EP) ...................... 15195365

(51) Int. Cl.
*A61B 5/1486* (2006.01)
*A61B 5/145* (2006.01)
*A61B 5/00* (2006.01)

(52) U.S. Cl.
CPC ...... *A61B 5/14865* (2013.01); *A61B 5/14532* (2013.01); *A61B 5/6801* (2013.01);
(Continued)

(58) Field of Classification Search
None
See application file for complete search history.

(56) References Cited

U.S. PATENT DOCUMENTS

| 5,413,690 A | 5/1995 | Kost et al. |
| 5,762,770 A | 6/1998 | Pritchard et al. |
(Continued)

FOREIGN PATENT DOCUMENTS

| CN | 103519827 | 1/2014 |
| DE | 954712 | 12/1956 |
(Continued)

*Primary Examiner* — Jay B Shah
(74) *Attorney, Agent, or Firm* — Woodard, Emhardt, Henry, Reeves & Wagner, LLP

(57) ABSTRACT

A sensor (110), a sensor assembly (256) for detecting at least one analyte in a body fluid and methods of manufacturing a sensor (110) and a sensor assembly (256) for detecting at least one analyte in a body fluid are disclosed. The sensor (110) has at least one substrate (114). The sensor (110) further has at least two electrodes (116) applied to the substrate (114), wherein the electrodes (116) are adapted for detecting the analyte. The sensor (110) further has at least two contact pads (118) applied to the substrate (114) and at least two electrical traces (120) applied to the substrate (114). The electrical traces (120) electrically connect the electrodes (116) and the contact pads (118). The sensor (110) further comprises a sealing ring (134) fixedly applied to the substrate (114). The sealing ring (134) surrounds the contact pads (118).

17 Claims, 11 Drawing Sheets

(52) U.S. Cl.
 CPC ... *A61B 2562/043* (2013.01); *A61B 2562/166* (2013.01); *A61B 2562/18* (2013.01)

(56) References Cited

U.S. PATENT DOCUMENTS

| | | |
|---|---|---|
| 5,798,031 A | 8/1998 | Charlton et al. |
| 6,129,823 A | 10/2000 | Hughes et al. |
| 6,360,888 B1 | 3/2002 | McIvor et al. |
| 2003/0222656 A1* | 12/2003 | Phillips ................ G01N 27/02 324/605 |
| 2005/0013731 A1 | 1/2005 | Burke et al. |
| 2007/0135697 A1 | 6/2007 | Reggiardo |
| 2008/0242962 A1 | 10/2008 | Roesicke et al. |
| 2011/0178378 A1* | 7/2011 | Brister ............... A61B 5/14503 600/309 |
| 2011/0319723 A1 | 12/2011 | Ziegler et al. |
| 2011/0319734 A1 | 12/2011 | Gottlieb et al. |
| 2012/0244043 A1 | 9/2012 | Leblanc et al. |
| 2013/0143420 A1* | 6/2013 | Light ..................... H01R 35/02 439/65 |
| 2014/0005492 A1 | 1/2014 | Harttig |
| 2014/0121989 A1* | 5/2014 | Kamath ................. G16Z 99/00 702/19 |
| 2015/0087942 A1 | 3/2015 | Brauker et al. |
| 2015/0099954 A1 | 4/2015 | Achmann et al. |

FOREIGN PATENT DOCUMENTS

| | | |
|---|---|---|
| DE | 20020566 U1 | 1/2002 |
| EP | 2 238 903 A1 | 10/2010 |
| EP | 2 238 903 | 2/2012 |
| EP | 2 532 305 | 12/2012 |
| RU | 2009132504 | 3/2011 |
| WO | WO 2007/071562 | 6/2007 |
| WO | WO 2011/041531 | 4/2011 |

\* cited by examiner

SENSOR AND SENSOR ASSEMBLY FOR DETECTING AN ANALYTE IN A BODY FLUID

FIELD OF THE INVENTION

The invention relates to a sensor and a sensor assembly for detecting at least one analyte in a body fluid. The invention further relates to methods of manufacturing a sensor and a sensor assembly for detecting at least one analyte in a body fluid. The devices and methods according to the present invention may mainly be used for long-term monitoring of an analyte concentration in a body fluid, such as for long-term monitoring of a blood glucose level or of the concentration of one or more other types of analytes in a body fluid. The invention may both be applied in the field of home care as well as in the field of professional care, such as in hospitals. Other applications are feasible.

RELATED ART

Monitoring certain body functions, more particularly monitoring one or more concentrations of certain analytes, plays an important role in the prevention and treatment of various diseases. Without restricting further possible applications, the invention will be described in the following text with reference to blood-glucose monitoring. However, additionally or alternatively, the invention can also be applied to other types of analytes.

Blood glucose monitoring, besides by using optical measurements, specifically may be performed by using electrochemical biosensors. Examples of electrochemical biosensors for measuring glucose, specifically in blood or other body fluids, are known from U.S. Pat. Nos. 5,413,690 A, 5,762,770 A, 5,798,031 A, 6,129,823 A or US 2005/0013731 A1.

In addition to so-called spot measurements, in which a sample of a body fluid is taken from a user in a targeted fashion and examined with respect to the analyte concentration, continuous measurements are increasingly becoming established. Thus, in the recent past, continuous measuring of glucose in the interstitial tissue (also referred to as continuous monitoring, CM) for example has been established as another important method for managing, monitoring and controlling a diabetes state.

In the process, the active sensor region is applied directly to the measurement site, which is generally arranged in the interstitial tissue, and, for example, converts glucose into electrical charge by using an enzyme (e.g. glucose oxidase, GOD), which charge is related to the glucose concentration and can be used as a measurement variable. Examples of such transcutaneous measurement systems are described in U.S. Pat. No. 6,360,888 B1 or in US 2008/0242962 A1.

Hence, current continuous monitoring systems typically are transcutaneous systems or subcutaneous systems, wherein both expressions, in the following, will be used equivalently. This means that the actual sensor or at least a measuring portion of the sensor is arranged under the skin of the user. However, an evaluation and control part of the system (also referred to as a patch) is generally situated outside of the body of the user, outside of the human or animal body. In the process, the sensor is generally applied using an insertion instrument, which is likewise described in U.S. Pat. No. 6,360,888 B1 in an exemplary fashion. Other types of insertion instruments are also known.

The sensor typically comprises a substrate, such as a flat substrate, onto which an electrically conductive pattern of electrodes, conductive traces and contact pads may be applied. In use, the conductive traces typically are isolated by using one or more electrically insulating materials. The electrically insulating material typically further also acts as a protection against humidity and other detrimental substances and, as an example, may comprise one or more cover layers such as resists.

As outlined above, in transcutaneous systems, a control part is typically required, which may be located outside the body tissue and which has to be in communication with the sensor. Typically, this communication is established by providing at least one electrical contact between the sensor and the control part, which may be a permanent electrical contact or a releasable electrical contact. Examples of electrical contacts for contacting a triangular assembly of contact pads are shown e.g. in DE 954712 B. Other techniques or providing electrical contacts, such as by appropriate spring contacts, are generally known and may be applied.

In order to avoid detrimental effects of the aggressive environment onto the conductive properties of the electrical contact, the region of the electrical contact is typically encapsulated and protected against humidity. Generally, encapsulations of electrical locks and contacts by using appropriate seals is known from e.g. DE 200 20 566 U1. Specifically in transcutaneous or subcutaneous sensors, in which the region of electrical contact between the sensor and the control part is close to the human skin, an efficient protection against humidity, dirt, sweat and detergents, such as detergents used for body care, is crucial.

US 2008/0242962 A1 discloses a system for in-vivo measurement of analyte concentrations. A sensor is part of a replaceable sensor carrier unit that comprises a sealed housing in which the sensor is disposed. A sealed housing of the sensor carrier unit protects the sensitive sensor from adverse environmental influences. Additionally, the housing of the sensor carrier unit locks to a base station in order to couple the sensor to a base station. The sensor can be exposed for insertion after coupling, for example by means of a predetermined breaking point for the sensor that is provided on the housing of the sensor carrier unit.

WO 2011/041531 A1 discloses systems and methods for providing a compressible interconnect for allowing electrical communication between an electronics unit and an analyte sensor in an on-body analyte monitoring device and for reducing the Z-height of an on-body analyte monitoring device by utilizing interconnects. Therein, the electronics unit comprises a seal disposed proximate an elongated interconnect. The seal is an individually molded component made of low duromer silicone, rubber or some other material TPE. In some embodiments, the interconnect extends approximately 1 mm beyond the face of the seal. When the electronics unit is locked into position, the interconnect compresses and makes contact with the conductive pads on the sensor. The seal also compresses to form a barrier around the perimeter of the interconnect/sensor connection. The interconnect may work without the seal, however once liquid or dust got in, the interconnect/sensor interface may be compromised and fail.

US 2015/0087942 A1 relates to systems and methods for transcutaneous measurement of glucose in a host. The device for measuring an analyte in a host comprises a sensor operably connected to sensor electronics, the sensor electronics configured for measuring an analyte in a host. At least one electrical contact is configured to connect the sensor to the sensor electronics and a sealing member at least partially surrounds the sensor and the electrical contact. Additionally an adhesive pad is placed over some or all of the sensor assembly such that after sensor insertion is complete adhesion is ensured and optionally to ensure an airtight seal or watertight seal around the wound exit-site (or sensor insertion site). The sealing member comprises a material selected from the group consisting of silicone, silicone-co-polyurethane, polyurethane, polysulfide, and mixtures thereof. The sealing member further comprises a sealant sandwiched between an upper portion of the sealing member and a lower portion of the sealing member.

In other fields of technology, such as the technical field of microfluidic devices, sealing may also be an issue, such as sealing against leaking of liquids. As an example, US 2012/0244043 A1 relates to gaskets for sealing fluid interfaces in micro fluidic systems. In particular, a microfluidic device includes at least one internal channel, and at least one port in fluid communication with the channel. A seal is associated with the port and is configured to receive a fluid transport mechanism. The seal can be formed from an elastomeric material that is compatible for use with fluorinated oil and resists flaking and degradation. In particular embodiments, the gasket is made of a thermoplastic silicone elastomer, such as Geniomer® 200 Silicone TPE (Wacker Chemie), which is a two phase block copolymer made up of a soft polydimethylsiloxane (PDMS) phase and a hard aliphatic isocyanate phase. Such materials are capable of resisting flaking and degradation in the presence of a fluorinated oil, and/or after sealingly receiving a means for introducing a sample fluid (e.g., a tubing or pipette).

Despite the advantages and the progress achieved by the above-mentioned developments, specifically in the field of continuous monitoring technology, some significant technical challenges remain. Thus, generally, known techniques for protecting and electrical contact between a sensor and a control part generally are rather complex. An assembly of a plurality of components is generally required, which typically implies a complex and costly manufacturing process. Further, known techniques generally require voluminous components, which is an issue, specifically considering the fact that miniaturizing the sensor assemblies is a factor contributing to the convenience of use. Specifically in case complex encapsulation parts manufactured by plastic molding techniques are required for protecting the electrical contacts, a rising of costs and sensor volume typically has to be taken into account. Further, cleaning of complex protective covers, such as protections including O-rings or other seals, turns out to be difficult. Still further, specifically when following the goal of miniaturization, the precision of available sealing elements such as O-rings is challenging, which typically necessitates costly selection processes.

Problem to be Solved

It is therefore an objective of the present invention to propose a sensor, a sensor assembly and method of manufacturing the sensor or sensor assembly, which at least partially avoid the short-comings of known devices and methods of this kind and which at least partially address the above-mentioned challenges. Specifically, devices and methods shall be disclosed which avoid complex and voluminous encapsulation techniques, which may be implemented in large-scale production processes and which are cost-efficient.

SUMMARY OF THE INVENTION

This problem is solved by a sensor, a sensor assembly, a method for manufacturing a sensor and a method of manufacturing a sensor assembly with the features of the independent claims. Preferred embodiments, which might be realized in an isolated fashion or in any arbitrary combination, are listed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of the present invention, a sensor for detecting at least one analyte in a body fluid, specifically for use as a transcutaneous sensor, is disclosed. The sensor comprises at least one substrate. The sensor further has at least two electrodes applied to the substrate, wherein the electrodes are adapted for detecting the analyte. The sensor further has at least two contact pads applied to the substrate and at least two electrical traces applied to the substrate. The electrical traces electrically connect the electrodes and the contact pads. The substrate may comprise one or more components, which fully or partially may cover one or more of the electrodes, the conductive traces or the contact pads. Thus, generally, the substrate may comprise a multilayer setup, wherein the electrodes, conductive traces and contact pads not necessarily have to be on an outer surface of the multilayer setup. Generally, however, the electrodes preferably may be fully or partially left open and uncovered or covered by one or more permeable materials, only. Similarly, the contact pads may be left open or may be covered by one or more electrically conductive materials, only. Thus, as an example, the conductive traces typically may be isolated by using one or more electrically insulating materials, such as one or more electrically insulating cover layers, which, as a definition, may form part of the substrate.

Consequently, the sensor may further comprise at least one electrically insulating material, which may form part of the substrate, and which may fully or partially, the conductive traces and which may at least partially leave open or leave free the electrodes and the contact pads. The electrically insulating material typically further also acts as a protection against humidity and other detrimental substances and, as an example, may comprise one or more cover layers such as resists.

The sensor further comprises a sealing ring fixedly applied to the substrate. In case the substrate comprises a plurality of components such as a multilayer setup, the sealing ring may be applied to one or more of the components. Thus, as an example, the substrate may comprise at least one base layer, such as at least one insulating base layer, to which one or more of the electrodes, the conductive traces all the contact pads may be applied. As outlined above, the substrate may further comprise at least one insulating material which fully or partially covers one or more of the electrodes, the conductive traces or the contact pads. As an example, the at least one insulating material may at least partially leave open the electrodes and the contact pads. The insulating material, as an example, may comprise one or more insulating layers fully or partially covering one or more of the electrodes, the conductive traces the contact pads, such as one or more insulating layers at least partially leaving open the electrodes and the contact pads. The sealing ring, as an example, may either be directly applied to the at least one insulating base layer of the substrate, such as to at least one insulating foil forming the base layer of the substrate, or to the at least one insulating material, such as the at least one insulating cover layer which fully or partially covers one or more of the electrodes, the conductive traces of the contact pads and which at least partially may leave open the electrodes and the contact pads. The sealing ring surrounds the contact pads.

As generally used within the present invention, the terms "patient" and "user" may refer to a human being or an animal, independent from the fact that the human being or animal, respectively, may be in a healthy condition or may suffer from one or more diseases. As an example, the patient or the user may be a human being or an animal suffering from diabetes. However, additionally or alternatively, the invention may be applied to other types of users or patients or diseases.

As further used herein, the term "body fluid" generally may refer to a fluid which typically is present in a body or body tissue of the user or the patient and/or which may be produced by the body of the user or the patient. As an example for body tissue, interstitial tissue may be named. Thus, as an example, the body fluid may be selected from the group consisting of blood and interstitial fluid. However, additionally or alternatively, one or more other types of body fluids may be used, such as saliva, tear fluid, urine or other body fluids. During detection of the at least one analyte, the body fluid may be present within the body or body tissue. Thus, specifically, as will be outlined in further detail below, the sensor may be configured for detecting at least one analyte in a body tissue.

As further used herein, the term "analyte" may refer to an arbitrary element, component or compound which may be present in the body fluid and the presence and/or the concentration of which may be of interest for the user, the patient or medical staff such as a medical doctor. Particularly, the analyte may be or may comprise an arbitrary chemical substance or chemical compound which may take part in the metabolism of the user or the patient, such as at least one metabolite. As an example, the at least one analyte may be selected from the group consisting of glucose, cholesterol, triglycerides, lactate. Additionally or alternatively, however, other types of analytes may be used and/or any combination of analytes may be determined. The detection of the at least one analyte specifically may be an analyte-specific detection.

As further used herein, the term "detect" generally refers to the process of determining the presence and/or the quantity and/or the concentration of the at least one analyte. Thus, the detection may be or may comprise a qualitative detection, simply determining the presence of the at least one analyte or the absence of the at least one analyte, and/or may be or may comprise a quantitative detection, which determines the quantity and/or the concentration of the at least one analyte. As a result of the detection, at least one signal may be produced which characterizes an outcome of the detection, such as at least one measurement signal. The at least one signal specifically may be or may comprise at least one electronic signal such as at least one voltage and/or at least one current. The at least one signal may be or may comprise at least one analogue signal and/or may be or may comprise at least one digital signal.

As further used herein, the term "determining a concentration" generally may refer to a process of generating at least one representative result or a plurality of representative results indicating the concentration of the analyte in the body fluid.

As further used herein, the term "sensor" may generally refer to an arbitrary element which is adapted to perform the above-mentioned process of the detection and/or which is adapted to be used in the above-mentioned process of the detection. Thus, the sensor specifically may be adapted to determine the concentration of the analyte and/or a presence of the analyte.

The sensor may particularly be a "transcutaneous sensor". As used herein, the term transcutaneous sensor generally refers to a sensor which is adapted to be fully or at least partly arranged within a body tissue of the patient or the user. For this purpose, the sensor generally may be dimensioned such that a transcutaneous insertion is feasible, such as by providing a width in a direction perpendicular to an insertion direction of no more than 5 mm, preferably of no more than 2 mm, more preferably of no more than 1.5 mm. The sensor may have a length of less than 50 mm, such as a length of 30 mm or less, e.g. a length of 5 mm to 30 mm. It shall be noted, however, that other dimensions are feasible. In order to further render the sensor to be usable as a transcutaneous sensor, the sensor may fully or partially provide a biocompatible surface, i.e. a surface which, at least during durations of use, do not have any detrimental effects on the user, the patient or the body tissue. As an example, the transcutaneous sensor may fully or partially be covered with at least one biocompatible membrane, such as at least one polymer membrane or gel membrane which is permeable for the at least one analyte and/or the at least one body fluid and which, on the other hand, retains sensor substances such as one or more test chemicals within the sensor and prevents a migration of these substances into the body tissue.

The sensor preferably may be an "electrochemical sensor". As used herein, an electrochemical sensor generally is a sensor which is configured to conduct an electrochemical measurement in order to detect the at least one analyte contained in the body fluid. The term "electrochemical measurement" refers to a detection of an electrochemically detectable property of the analyte, such as an electrochemical detection reaction. Thus, for example, the electrochemical detection reaction may be detected by comparing one or more electrode potentials, as further discussed below. The electrochemical sensor specifically may be adapted to and/or may be usable to generate at least one electrical sensor signal which directly or indirectly indicates the presence and/or the extent of the electrochemical detection reaction, such as at least one current and/or at least one voltage. For this purpose, as will be outlined in further detail below, the at least one electrochemical sensor provides two or more electrodes, which also are referred to as a sensor electrodes. The detection may be analyte-specific. The measurement may be a qualitative and/or a quantitative measurement. Still, other embodiments are feasible.

As further used herein, the term "electrode" may generally refer to an arbitrary element which is configured to or which is usable to electrically or electrochemically detect the analyte. Specifically, each electrode may comprise at least one conductive pad or conductive element, such as at least one metal pad and/or at least one metal element and/or at least one pad or element made of at least one conductive inorganic or organic material such as carbon and/or a conductive polymer. The at least one conductive pad or conductive element may be uncovered and/or may be covered with at least one additional material, such as at least one sensor chemical, as will be outlined in further detail below. The at least two electrodes of the sensor may be embodied such that an electrochemical reaction may take place at one or more of the electrodes, such as one or more working electrodes. Thus, the electrodes may be embodied such that an oxidation reaction and/or reduction reaction may take place at one or more of the electrodes. The electrochemical detection reaction may be detected by comparing one or more electrode potentials, such as an electrostatic potential of a working electrode with an electrostatic potential of one or more further electrodes such as a counter electrode or a reference electrode. Generally, the two or more electrodes may be used for one or more of an amperometric, an amperostatic, a potentiometric or a potentiostatic measurement. These types of measurements generally are known to the skilled person in the art of analyte detection, such as from WO 2007/071562 A1 and/or the prior art documents disclosed therein. For potential setups of the electrodes, electrode materials or measurement setups, reference may be made to this document. It shall be noted, however, that other setups, electrode materials or measurement setups may be used within the present invention.

The at least two electrodes may comprise at least one working electrode. As used herein, the term "working electrode" refers to an electrode being adapted for or being usable for performing at least one electrochemical detection reaction for detecting the at least one analyte in the body fluid. The working electrode may have at least one test chemical being sensitive to the analyte to be detected. The working electrode may further comprise at least one conductive working electrode pad. The conductive working electrode pad may be in contact with the at least one test chemical. Thus, the at least one test chemical may be coated onto the at least one conductive working electrode pad. The at least one test chemical may form at least one test chemical surface which may be in contact with the at least one body fluid. As an example, the at least one test chemical surface may be an open test chemical surface or may be covered by the above-mentioned at least one membrane which is permeable to the at least one analyte to be detected and/or to the body fluid or a part thereof, such that the analyte may interact with the test chemical. For potential test chemicals and/or materials for the conductive working electrode pad, again, reference may be made to WO 2007/071562 A1 and/or the prior art documents disclosed therein. Other embodiments, however, are feasible.

The one or more "working electrode pads" specifically may be formed by at least one dot, line or grid which each can form a coherent area of an electrode material. If more than one dot, line or grid of the electrode material is superimposed, the sensor may provide more than one electrode pad. All electrode pads together may build the working electrode. The sensor may comprise the working electrode with a number of electrode pads in a range from 1 to 50, preferably from 2 to 30, preferably from 5 to 20 electrode pads.

The term "test chemical" specifically may refer to an arbitrary material or a composition of materials adapted to change at least one detectable property in the presence of at least one analyte. This property may be an electrochemically detectable property. Specifically, the at least one test chemical may be a highly selective test chemical, which only changes the property if the analyte is present in the body fluid whereas no change occurs if the analyte is not present. The degree or change of the at least one property is dependent on the concentration of the analyte in the body fluid, in order to allow a quantitative detection of the analyte. As an example, the test chemical may comprise at least one enzyme, such as glucose oxidase and/or glucose dehydrogenase.

The at least two electrodes may further comprise at least one counter electrode. As used herein, the term "counter electrode" refers to an electrode adapted for performing at least one electrochemical counter reaction and adapted for balancing a current flow required by the detection reaction at the working electrode.

Additionally or alternatively the at least two electrodes may further comprise at least one reference electrode. The reference electrode may have a stable and well-known electrode potential. The electrode potential may preferably be highly stable. The counter electrode and the reference electrode may be one of a common electrode or two separate electrodes.

Again, for potential materials usable for the counter electrode and/or the reference electrode, reference may be made to WO 2007/071562 A1 and/or the prior art documents disclosed therein. Other embodiments, however, are feasible.

The electrodes, particularly the working electrode, the counter electrode and/or the reference electrode, may have the identical dimension. The term "dimension" refers to one or more of a width, a length, a surface area, a shape of the first and the second electrodes. A shape of the electrodes may be determined by a manufacturing process, such as a cutting and/or a printing process. The shape may be rectangular or round. Still, other embodiments are feasible, such as embodiments in which the dimensions of the working electrode and the counter/reference electrodes differ and/or embodiments in which a non-circular shape or a non-rectangular shape is used. The electrodes may be made of a non-corrosive and non-passivating material. With regard to possible electrode materials, reference may be made to the prior art documents cited above.

As further used herein, the term "substrate" may generally refer to an arbitrary element which is suitable to carry one or more other elements disposed thereon or therein. As an example, the substrate may be a flat substrate, such as a substrate having a lateral extension exceeding its thickness by at least a factor of 2, at least a factor of 5, at least a factor of 10, or even at least a factor of 20 or more.

The substrate specifically may have an elongated shape, such as a strip-shape and/or a bar-shape. The substrate, as an example, may comprise a shaft, specifically a shaft having an elongate shape. For example the shaft may have a shape selected from the group consisting of a strip, a needle, a tape.

The substrate may comprise at least one contact portion. The contact portion may be connected mechanically and/or electrically to at least one control part of the sensor assembly comprising the sensor, specifically to a body mount of the control part and/or to an electronics unit of the control part. The contact portion may be widened as compared to the remaining substrate, particularly compared to the shaft. The contact portion may preferably be a rectangular contact portion. Other shapes are feasible, however. Thus, the contact portion may have a shape selected from the group consisting of: round, oval, angular. Still, other embodiments are feasible.

The substrate, as outlined above, may be an elongate substrate, with the electrodes being placed at one end of the elongate substrate and the contact pads being placed on an opposing end of the substrate. The contact pads may be located in the contact portion.

The substrate may be a flexible substrate, i.e. a substrate which may be bent or deformed by forces which usually occur during wearing and insertion into the body tissue, such as forces of 10 N or less. Specifically the substrate may be made of or may contain at least one deformable material, such as at least one plastic or malleable material and/or at least one elastic material. As an example, the substrate may be or may comprise at least one foil, such as at least one foil made of one or more of a paper material, a cardboard material, a plastic material, a metal material, a ceramic material or a glass material. As an example, the substrate may comprise at least one polyimide foil. The substrate specifically may comprise at least one electrically insulating material, such as at least one electrically insulating plastic foil.

As used herein, the term "contact pad" generally refers to an element having an open or electrically contactable surface which is electrically conductive. As an example, the contact pads may be or may comprise at least one layer of at least one electrically conductive material which directly or indirectly may be deposited onto the substrate and which provides an electrically contactable surface. In a dimension or direction parallel to a surface of the substrate, the contact pads may provide a contact surface area, such as an area having a rectangular shape, a polygonal shape or a round shape. Other shapes are possible.

The contact pads may be located in the above-mentioned contact portion of the sensor. The contact pads may be fully or at least partially made of at least one metallic material. Thus, as an example, contact pads may comprise at least one gold layer. In addition or alternatively, other types of metal layers may be applied, such as at least one of: Cu, Ni, Ag, Au, Pd, Pt. Again, additionally or alternatively, the contact pads may fully or partially be made of at least one non-metallic electrically conductive material, such as at least one of: a conductive carbon material, such as graphite, graphene, carbon nanotubes, glassy carbon; an electrically conductive organic material, such as an electrically conductive polymer.

As further used herein, the term "electrical trace" may generally refer to an arbitrary electrically conducting element which is suited or configured to electrically connect at least two electrical elements, such as, in this case, at least one contact pad with at least one associated electrode. Thus, for each electrode, at least one contact pad may be associated and the electrode and the associated contact pads may be connected via the at least one electrical trace, thereby allowing for electrically contacting, independently, each electrode via the at least one associated contact pad. The electrical traces specifically may have a shape at least in two dimensions. The electrical trace preferably may have an elongated shape, such as a length along the substrate exceeding a width in a plane of the substrate by at least a factor of 5, such as at least a factor of 10, or even at least a factor of 100. For example, the electrical trace may comprise at least one wire or path. Furthermore, the electrical trace may comprise at least one electrically conductive material. Preferably, the electrically conductive material may comprise copper. Additionally or alternatively, one or more of the materials listed above for the contact pads may be used. Further, the electrically conductive material may be or may comprise at least one material selected from the group consisting of: an electrically conductive organic material, preferably at least one electrically conductive polymer, an electrically conductive carbon material, preferably one or more of graphite, graphene, glassy carbon and carbon nanotubes; a metal preferably from the group consisting of Cu, Ni, Ag, Au, Pd and Pt. However, additionally or alternatively, one or more other electrically conductive materials may be used.

The sensor may further comprise at least one electrically insulating material. As further used herein, the term "electrically insulating material" may generally refer to a material having an electric conductivity below 0.001 S/cm, preferably below 0.0001 S/cm, most preferably below $10^{-6}$ S/cm, even more preferably below $10^{-8}$ S/cm, below $10^{-9}$ S/cm, below $10^{-10}$ S/cm or even below $10^{-11}$ S/cm. For example the electrically insulating material may comprise an insulating resist. However, other materials are feasible. The electrically insulating material may at least partially cover the electrical traces, the insulating material leaving open the electrodes and the contact pads. The electrically insulating material may comprise at least one insulating cover layer covering the electrical traces. The electrically insulating material may form openings, wherein the electrodes are located within the openings.

The electrically insulating material may at least not fully cover the contact portion. The electrically insulating material may be distinct from the sealing ring. The sealing ring may exceed the electrically insulating material, specifically at least one insulating layer may be formed by the electrically insulating material, in height, preferably by at least a factor of 1.5, more preferably by at least a factor of 2. Thus, the at least one sealing ring specifically may protrude from the surface of the sensor and/or the sensor substrate and/or from a surface of the at least one electrically insulating material covering the sensor and/or the sensor substrate. The sealing ring may be fully or partially applied onto the electrically insulating material.

As further used herein, the term "sealing ring" may generally refer to an arbitrary element which is configured to surround one or more elements to be sealed off from environmental influences such as moisture. Specifically, the sealing ring may be configured to surround the at least one element to be sealed off from the environmental influences in at least two dimensions. Thus, the sealing ring may be a ring-shaped element. The ring-shaped element may have the shape of a circular ring, a polygonal ring, an oval ring or any other closed shape. The sealing ring specifically may be made of at least one compressible material.

As further used herein, the term "fixedly applied" generally refers to the fact that the sealing ring contacts the substrate and is mounted onto the substrate in such a way that the sealing ring does not come off the substrate without exerting additional forces to the sealing ring and/or the substrate in order to remove these elements from each other, such as additional forces exceeding the gravitational force. Specifically, the sealing ring may be adhered to the substrate by material engagement, such as by directly gluing the sealing ring to the substrate. Specifically, the sealing ring itself may be made of an adhesive material which directly adheres to the substrate, thereby fixedly applying the sealing ring to the substrate by adhesive forces. Thus, specifically, no additional adhesive material between the sealing ring and the substrate may be used, and the sealing ring may directly contact the substrate.

As outlined above, the sealing ring surrounds the contact pads. As an example, the contact pads may be located on a surface of the substrate and/or of the sensor, such as in a contact portion of the substrate. The sealing ring may also be located on this surface, specifically in the contact portion of the substrate. As outlined above, therein, the sealing ring may directly contact the substrate and/or may contact at least one insulating material interposed in between the substrate and the sealing ring. The sealing ring may shield an interior of the sealing ring from an ambient atmosphere, prevent leakage and/or exclude contamination and/or moisture. The contact pads commonly may be located as a group on a surface of the substrate and the sealing ring commonly may surround the group.

The sealing ring may comprise at least one of an organic material, a silicone or a plastic material. Specifically, the at least one sealing ring may comprise at least one polymer, including the option of the polymer comprising at least one silicone material. Thus, the sealing ring may comprise at least one elastomer. The elastomer may comprise at least one silicone material, preferably at least one silicone and/or a silicone polymer. The elastomer preferably may comprise at least one silicone copolymer, preferably a copolymer of dimethylsiloxane, more preferably a copolymer of dimethylsiloxane and urea. For example, the elastomer may comprise at least one urea copolymer. The elastomer may be a thermoplastic elastomer or a cured elastomer. As a commercial example of a material or group of materials usable for the sealing ring, Geniomer® materials available by Wacker Chemie AG, Munich, Germany, may be used, which form a group of poly(dimethylsiloxane)-polyurea copolymers. As an example, Geniomer® 110, Geniomer® 145, or Geniomer® 345 or mixtures thereof may be used. In a cured state, the sealing ring generally may have a Shore A hardness of e.g. 5 to 150, such as 10 to 100, 20 to 90, or 25 to 85. It shall be noted, however, that other materials and/or other hardness are feasible. The named range of hardnesses, however, turned out to be favorable for the specified purposes.

The sealing lip may have a maximum height perpendicular to a surface of the sensor of e.g. 20 µm to 300 µm, such as 50 µm to 200 µm or 80 µm to 150 µm, e.g. 100 µm. Other thicknesses, however, are feasible.

The sealing ring may directly be applied to the substrate, which includes the option that the substrate is fully or partially covered by at least one insulating material, such as at least one insulating resin or resist, which generally may form part of the substrate.

The sealing ring specifically may be producible by applying a liquid or pasty sealing material to the substrate, including the option that the liquid or pasty sealing material is applied to at least one insulating material fully or partially covering the substrate and, thus, by definition may form part of the substrate itself. The liquid or pasty sealing material may be fully or partially hardened after application, such as by one or more of drying, the operation of at least one solvent removal, chemical hardening or polymerization, photo curing or other ways of hardening. After hardening, the formerly liquid or pasty sealing material still may have a deformable shape and/or still may be compressible, in order to provide the above-mentioned sealing properties and in order to be compressed when pressed onto a surface.

The sealing ring may have a shape exemplarily selected from the group consisting of: a circular shape, an oval shape, a polygonal shape, a rectangular shape. However, the sealing ring may generally have an arbitrary shape. Further, the sealing ring may generally have an arbitrary cross-section, such as a rectangular cross-section and/or rounded cross-section and/or a polygonal cross-section. However, other types of cross-sections may be applied alternatively.

The sealing ring may further have a constant thickness. Thus, the sealing ring may define a closed sealing line along which the sealing ring contacts and element such as a flat element onto which the substrate is pressed. Along this sealing line, the sealing ring may have a constant thickness, with a tolerance of variation of e.g. no more than 20% or no more than 10%. However, other embodiments are feasible.

The sealing ring may comprise at least one sealing lip. Thus, in a cross-sectional view perpendicular to the sealing element and/or perpendicular to a surface of the sensor and/or the substrate, the sealing ring may define a cross-sectional profile with at least one, such as exactly one, maximum such as a local maximum. Thus, the profile may provide a maximum which defines the sealing lip. Thus, generally, as used herein, the term "sealing lip" may refer to a maximum in a cross-sectional profile of the sealing ring, which, when the sensor with the sealing ring thereon is pressed onto another surface, is the first part of the sealing ring to contact the other surface. The profile itself may be symmetric or asymmetric in shape, wherein an asymmetric profile may be favorable. Therein, the maximum height may be closer to an inner or outer perimeter of the sealing ring.

In a further aspect of the present invention, a sensor assembly for detecting at least one analyte in a body fluid is disclosed. As used herein, an "assembly" generally refers to a group of at least two elements which may interact in order to fulfill at least one common function. The at least two components may be handled independently or may be coupled, connectable or integratable in order to form a common component. Thus, a "sensor assembly" generally refers to a group of at least two elements or components which are capable of interacting in order to perform at least one sensor function, in the present case in order to perform at least one detection of the at least one analyte in the body fluid and/or in order to contribute to the at least one detection of the at least one analyte in the body fluid. The sensor assembly generally may also be referred to as a sensor system, a sensor kit or a sensor device.

The sensor assembly comprises at least one sensor according to the present invention, such as according to at least one of the embodiments disclosed above or as further described below.

The sensor assembly may particularly be a transcutaneous sensor system wherein the sensor is wholly or at least partly arranged within the body tissue of the patient or the user. At least one component of the sensor system may be wholly or partly outside of the body tissue, for example the control part. The sensor may be interconnected through a tissue surface or skin of the patient or the user. Thus, the sensor may partially be inserted into the body tissue, such as with a sensor portion of the sensor, and partially may be located outside the body tissue, such as with a connector portion of the sensor. Still, other embodiments are feasible.

The sensor assembly further comprises at least one control part having at least one electronics unit for one or more of controlling the detection of the analyte or transmitting measurement data to another component. The control part, preferably the electronics unit of the control part, comprises at least two electrical contacts. The electrical contacts are electrically connected to the contact pads of the sensor.

As used herein, the term "control part" may generally refer to an arbitrary component of the sensor assembly, which is designed to actuate the sensor and/or record signals from the sensor and/or evaluate these signals in whole or part. The control part may be designed to mechanically hold the sensor and to electrically contact the sensor.

As outlined above, the control part comprises at least one electronics unit. The control part may further comprise at least one body mount adapted for being mounted to the skin of the user. Thus, the sensor assembly may comprise the sensor and the control part, the control part comprising the electronics unit and the body mount.

As used herein, the term "electronics unit" generally refers to an arbitrary device having at least one electronic component. Specifically, the electronics unit may comprise at least one electronic component for one or more of performing a measurement with the sensor, performing a voltage measurement, performing a current measurement, recording sensor signals, storing measurement signals or measurement data, transmitting sensor signals or measurement data to another device. Other embodiments of the electronic components are feasible. The electronics unit specifically may comprise at least one circuit board having disposed thereon at least one electronics component, such as at least one active and/or at least one passive component. The electronics unit may further comprise at least one housing which fully or partially surrounds the electronics component. The electronics unit may further comprise at least one of an integrated circuit, a microcontroller, a computer or an application-specific integrated circuit (ASIC). The electronics unit may specifically be embodied as a transmitter or may comprise a transmitter, for transmitting data. Preferably, the electronics unit may be reversibly connectable to the body mount.

As further used herein, the term "body mount" generally refers to a device which is attachable to the skin of the user or patient. Thus, the body mount may comprise at least one attachment component which is capable of connecting the body mount to the skin, such as at least one adhesive surface and/or at least one adhesive strip or plaster. The body mount may further comprise at least one body mount housing which may be used as a sensor support, for attachment of the sensor, such as the contact portion of the sensor. Thus, generally, the body mount may also be referred to as a sensor support. The electronics unit may be connectable to the body mount via at least one connection element, preferably releasably or reversibly, such as by using at least one clamping element, lever or the like, as will be explained in further detail below.

The control part, as outlined above, comprises at least two electrical contacts. The at least 2 electrical contacts specifically may be part of the at least one electronics unit of the control part. As used herein, the term "electrical contacts" may generally refer to arbitrary electrically conductive elements or ports which may interact electrically with the contact pads of the sensor, such that an electrical current may flow from the electrical contacts to the contact pads of the sensor or vice versa. The electrical contacts may simply comprise fields or layers of a conductive material, such as one or more of the conductive materials disclosed above in the context of the contact pads of the sensor. Additionally or alternatively, however, the electrical contacts may comprise mechanical elements such as one or more springs or the like. In the following, however, it is assumed that the electrical contacts of the control part are made of contact pads, i.e. fields or layers of a conductive material directly or indirectly applied to or integrated into at least one surface of the control part, specifically of the electronics unit of the control part.

The electrical contacts may preferably contact the contact pads of the sensor directly. Preferably the electrical contacts may not contact the sensor via a bonded connection. As further used herein, the term "bonded connection" may refer to any method where two or more elements are joined, such that flexibility between the two or more elements is completely or at least partially reduced. For example, such a method may comprise soldering or bonding and/or any other electrical and mechanical connection based on material engagement. Thus, as an example, the electrical contacts may simply be pressed onto the contact pads of the sensor or vice versa.

The control part may further comprise at least one housing. The housing specifically may be part of the electronics unit and may fully or partially encase the electronics unit. As an example, the electronics unit may comprise at least one circuit board, such as a printed circuit board, which, on one side, is fully covered by a housing, such as a round housing. The term "housing" may generally refer to an arbitrary element which is adapted to surround one or more elements in order to provide one or more of a mechanical connection protection, an environmental protection against moisture and/or ambient atmosphere, a shielding against electromagnetic influences or the like. Specifically, the housing may be configured to shield one or more elements of the sensor assembly from external influences like moisture and/or mechanical stress. The housing may be a watertight housing having an essentially round shape. Further, the housing may have an essentially flat surface. Specifically, the electronics unit may comprise an essentially flat base and the housing. The housing may cover the essentially flat base on a side opposing the body mount. The base may protrude from the housing, forming a rim which fully or partially surrounds the electronics unit. The rim may be configured to be engaged by the body mount. The housing, in general, may comprise one or more parts.

As outlined above, the electronics unit may be attachable to the body mount, such as reversibly and/or releasably. For this purpose, the control part, specifically the body mount, may comprise one or more locking mechanisms. Thus, the body mount may include a locking mechanism having at least one lever pivotably mounted to the body mount. Specifically, the lever may be pivotably attached to one end of the body mount. The lever may be permanently mounted to the body mount. By use of the lever, the electronics unit may be releasably locked to the body mount.

As used herein, the term "lever" may generally refer to a mechanical element comprising an elongated arm, also referred to as a lever arm, which is pivotably mounted to at least one hinge or fulcrum.

The locking mechanism specifically may be or may comprise a self-locking mechanism. As used herein, a "self-locking mechanism" generally refers to a mechanism which has at least one locked state and at least one unlocked state, wherein the mechanism, once brought into the locked state, is configured to maintain the locked state, such as by exerting forces onto at least one locking element of the self-locking mechanism in order to maintain this locking element in the locked position or locked state.

The lever specifically may be or may comprise at least one self-locking lever. As used herein, the term "self-locking" lever generally refers to a lever which is configured to hold, in a closed state or closed position, at least one element to be held in a fixed position, wherein, in the closed state or closed position, the element to be held exerts a force onto the self-locking lever which keeps the self-locking lever in the closed state or closed position. The self-locking specifically may be provided using an elastic swing placed behind a pivot point of the lever.

The lever, specifically the self-locking lever, may be or may comprise at least one knee lever. As used herein, the term "knee-lever" generally refers to a lever which, besides the lever arm and the hinge, comprises at least one protrusion protruding from the lever arm which is configured to exert a force onto and/or to interact with at least one element during a movement of the lever arm. The protrusion may be fixedly mounted to the lever arm, may be integrated into the lever arm or may probably be connected to the lever arm.

The lever, such as the lever arm, may have a generally arbitrary shape. Specifically, the lever, such as the lever arm, may have a round or bent shape, specifically in order to comply with a rounded outer shape of a housing of the control part, specifically the electronics unit. Thus, the lever arm specifically may have a curvature which, at least in part, corresponds to a curvature of a housing of the control part, specifically of the electronics unit of the control part, such that the lever arm, in a closed state, may be located on top of the housing.

The sensor assembly may further comprise at least one pressure element. As used herein, the term "pressure element" refers to an arbitrary element which is configured for pressing one element onto another element or vice versa. Specifically, the pressure element may be one or both of flexible or deformable. Thus, the pressure element may comprise at least one flexible or deformable material, such as at least one layer of flexible and/or deformable material.

The pressure element may comprise at least one of: an elastomer; a foam; a textile; a spring element; a thermoplastic polymer. The pressure element may be located in between a surface of the body mount and the sensor. The pressure element may be part of the control part. Thus, specifically, the pressure element may be part of the body mount and/or may be attached to the body mount. Additionally or alternatively, the pressure element may be attached to a surface of the sensor, specifically on a side of the sensor facing away from the electronics unit and/or from the electrical contacts of the electronics unit.

The pressure element may be located on a first side of the sensor, such as on a first side of the substrate of the sensor, and the sealing ring may be located on an opposing, second side of the sensor, such as of the substrate of the sensor. Therein, the pressure element may be attached to the sensor or may simply be pressed onto the sensor, whereas, as outlined above, the sealing ring is attached to the sensor. Thus, the pressure element and the sealing ring may be located on opposing sides of the sensor in the sensor assembly. Therein, the sealing ring may face the electronics unit and the electrical contacts, and the pressure element may be located facing away from the electronics unit.

The pressure element may be fully or partially integrated into a base of the body mount, such as by multicomponent injection molding.

The pressure element, on at least one surface, specifically on at least one surface facing the sensor, may comprise one or more cavities capable of acting as suction cups. The term "cavity" may refer to an arbitrary void volume within a surface, such as the surface of the pressure element. The cavities may be configured to adhere to an arbitrary surface, specifically by creating a partial vacuum. The partial vacuum may be created through a negative fluid pressure of a surrounding medium.

In a further aspect of the present invention, a method of manufacturing a sensor for detecting at least one analyte in a body fluid, preferably a sensor according to any embodiment as described above or as will further be described below, and a method of manufacturing a sensor assembly for detecting at least one analyte in a body fluid, specifically a sensor assembly according to any embodiment as described above or as will further be described below, are disclosed.

The methods comprise the method steps as given in the independent claims and as listed as follows. The method steps may be performed in the given order. However, other orders of the method steps are feasible. Further, one or more of the method steps may be performed in parallel and/or in a timely overlapping fashion. Further, one or more of the method steps may be performed repeatedly. Further, additional method steps may be present which are not listed.

The method of manufacturing the sensor comprises the following steps:
  providing at least one substrate;
  applying at least two electrodes to the substrate;
  applying at least two contact pads to the substrate;
  applying at least two electrical traces to the substrate, the electrical traces interconnecting the contact pads and the electrodes; and
  applying at least one sealing ring fixedly to the substrate, wherein the sealing ring surrounds the contact pads.

The step of providing the at least one substrate may, as an example, comprise a plurality of sub steps. As an example, as outlined above, the substrate may comprise a plurality of components, such as a multilayer setup. One or more of the components of the substrate may be provided after one or more of the steps of applying the at least two electrodes, the at least two contact pads and the at least two electrical traces, such as by covering one or more of these components with one or more electrically insulating materials which, as outlined above, may form part of the substrate. Thus, the step of providing the at least one substrate may, as a substep, comprise at least one step of applying at least one electrically insulating material, such as at least one electrically insulating cover layer, which, as an example, may fully or partially cover one or more of the electrodes, the conductive traces or the contact pads, such as by at least partially leaving open the electrodes and the contact pads.

The sensor specifically may be embodied as outlined above, according to one or more of the embodiments listed above or listed in further detail below. It shall be noted, however, that other embodiments are feasible.

For potential embodiments of application techniques for applying one or more of the electrodes, the contact pads or the electrical traces, reference may be made to common techniques such as techniques used in manufacturing printed circuit boards and/or used in manufacturing semiconductor devices. As an example, in case conductive material such as metals are applied for manufacturing one or more of the electrode pads of the electrodes, the contact pads on the electrical traces, one or more of chemical vapor deposition, physical vapor deposition, galvanic techniques or the like may be used. The elements may be deposited or applied in a patterned fashion, such as by using appropriate patterning techniques like printing, or may firstly be deposited in a non-patterned fashion and may be patterned later on, such as by laser patterning and/or by the lithographic techniques and/or etching techniques. These techniques generally are known to the skilled person. Further, as outlined above, at least one sensor chemical or detector chemical may be applied onto at least one of the electrodes, such as onto the working electrode, by known techniques, such as by printing techniques. Other embodiments are feasible.

The step of applying the at least one sealing ring fixedly to the substrate, including the option of applying the at least one sealing ring onto at least one insulating material such as onto at least one insulating layer covering the substrate and, thus, forming part of the substrate, may comprise applying at least one sealing material, preferably in a liquid or pasty form, to the substrate. The sealing material, specifically, may be applied in a patterned or structured fashion, by using at least one patterned or structured application technique, such as printing and/or dispensing. Other techniques, however, are feasible.

The sealing material may comprise at least one of a polymer material, a plastic material or a precursor material capable of cross-linking and/or polymerizing. Specifically, the sealing material may comprise a solution of at least one matrix material in at least one solvent, such as at least one of a polymer matrix material, a precursor matrix material or the like. As further used herein, the term "pasty form" may refer to an arbitrary suspension of particles and/or granular material in an arbitrary fluid. The sealing material in the pasty form may particularly behave as a solid until a sufficiently large load or stress is applied, i.e. may have thixotropic properties. The sealing material specifically may be a hardenable or curable material which may undergo at least one hardening step in order to fully or partially cure or harden the sealing material the hardening step, which may be part of the method, may imply at least one of a drying step, a curing step, a photo curing step, a thermal curing step, a chemical curing step, a step of evaporating at least one solvent, a cross-linking step. Other ways of hardening are feasible. After hardening, the sealing material still may have flexible or deformable properties, such as by providing the above-mentioned Shore hardness disclosed in the context of the sealing ring above.

The step of applying the at least one sealing ring fixedly to the substrate may further comprise applying the at least one sealing material to the substrate in a patterned fashion. The term "pattern" may specifically refer to a regularity in a distribution of the sealing material on the substrate. Specifically, the sealing material may be applied in a ring shape, such as by applying the sealing material as a closed line onto the substrate. For example the sealing material may be applied in a plurality of drops with a constant distance to each other. However, other embodiments are feasible. Additionally or alternatively, other ways of application may be feasible, such as a continuous application by continuous dispensing and/or by using one or more printing methods.

The step of applying the at least one sealing ring fixedly to the substrate may comprise at least one application method selected from the group consisting of: a printing method, preferably a printing method selected from the group consisting of a screen printing, a stencil printing, an inkjet printing or an offset printing; a dosing method using at least one dosing head, preferably a dosing needle, including the option of using at least one dispenser and/or at least one dispensing method by using at least one dispenser head. The term "screen printing" may generally refer to a printing technique wherein a mesh is used to transfer the sealing material to the substrate, expect in areas made impermeable to the sealing material by a blocking stencil. Generally, a blade may be moved across the mesh to fill openings of the mesh with the sealing material. The term "stencil printing" may generally refer to a printing technique, wherein the sealing material is transferred to the substrate via an arbitrary stencil or template. The stencil may produce a pattern of the sealing material on the surface. The screen printing and the stencil printing may particularly be applied in a combined fashion. The term "inkjet printing" may generally refer to an arbitrary printing technique, wherein droplets of the sealing material are propelled onto the substrate. The inkjet printing may comprise continuous printing and/or drop on demand printing. The term "offset printing" may generally refer to a printing technique, wherein the pattern of the sealing material is transferred from an arbitrary element, i.e. a plate, to the substrate. The term "dispensing" generally refers to a technique of applying a liquid or pasty material onto a substrate by using at least one hollow needle or capillary.

The step of applying the at least one sealing ring fixedly to the substrate may comprise at least one curing step. The term "curing" generally may refer to a process wherein a material, specifically a polymer material or a polymer precursor, may fully or partially toughen, cure or harden, particularly by one or more of the above-mentioned techniques, such as fully or partially evaporating one or more solvents, cross-linking of polymer chains, by heat and/or in presence of chemical additives and/or electron beams. Consequently, in the curing step the sealing material may be fully or partially hardened. Particularly, the curing step may comprise at least one of: a thermal curing, preferably one or both of a cooling or heating; a curing by evaporating at least one solvent, preferably by the using of vacuum; a photo curing, a chemical curing. The curing step may comprise one or more of a hardening by cooling of the sealing material or a curing by chemical cross-linking of the sealing material.

The method of manufacturing the sensor assembly comprises the following steps:
providing a sensor for detecting the at least one analyte in the body fluid, the sensor having at least one substrate, the sensor further having at least two electrodes applied to the substrate, the electrodes being adapted for detecting the analyte, the sensor further having at least two contact pads applied to the substrate and at least two electrical traces applied to the substrate, the electrical traces electrically connecting the electrodes and the contact pads, wherein the sensor further comprises a sealing ring fixedly applied to the substrate, the sealing ring surrounding the contact pads;
providing at least one control part, specifically a control part having at least one electronics unit, having at least one electronic component for one or more of controlling the detection of the analyte or transmitting measurement data to another component, wherein the control part comprises at least two electrical contacts; and
electrically connecting the electrical contacts to the contact pads of the sensor.

As outlined above, the substrate may comprise at least one electrically insulating material which at least partially leaves open the electrodes and the contact pads. As discussed above, the sealing ring may fixedly be applied to one or more components of the substrate, such as to at least one base layer of the substrate, specifically in insulating base layer, and/or two the above-mentioned electrically insulating material which at least partially leaves open the electrodes and the contact pads.

The sensor specifically may be embodied according to the present invention, such as according to one or more of the embodiments disclosed above or disclosed in further detail below. Thus, for definitions and optional details of the sensor, reference may be made to the disclosure of the sensor above or below. Similarly, for optional definitions and/or optional embodiments of the electronics unit, reference may be made to one or more of the embodiments disclosed above or disclosed in further detail below.

The step of electrically connecting the electrical contacts of the control part to the contact pads of the sensor may imply pressing the contact pads of the sensor on the electrical contacts of the control part or vice versa. As outlined above, specifically, no additional step of bonding and/or material engagement in between the contact pads of the sensor and the electrical contacts of the control part may be performed, specifically no additional step of soldering or applying an electrically conductive glue.

For potential embodiments of the control part, reference may be made to the disclosure and to the options given above or given in further detail below. Specifically, the control part may comprise at least one body mount having a surface mountable to a skin of a user and at least one electronics unit, also referred to as an electronics component, for one or more of controlling the detection of the analyte or transmitting measurement data to another component. The electronics unit may have the electrical contacts of the control part which electrically contact the sensor. Additionally or alternatively, however, the body mount may have the electrical contacts of the control part which electrically contact the sensor, wherein, in the latter case, an electrical connection between the body mount and the electronics unit may be established.

The step of electrically connecting the electrical contacts of the control part to the contact pads of the sensor may comprise the following sub-steps:
  mounting the sensor to the body mount such that contact pads of the sensor are facing away from the body mount; and
  mounting the electronics unit to the body mount such that the electrical contacts of the electronics unit are pressed against contact pads of the sensor or vice versa.

The step of mounting the sensor to the body mount may imply a mechanical mounting, only, without an electrical connection between the contact pads of the sensor and the body mount. Thus, the mechanical mounting may simply imply attaching the sensor to the body mount such that the body mount holds the sensor in place, with e.g. the contact pads of the sensor facing away from the body mount, such as facing upwards, towards the electronics unit.

The step of mounting the electronics unit to the body mount may, thus, imply both a mechanical mounting of the electronics unit to the body mount such that the electronics unit is held in place mechanically by the body mount or vice a versa, thereby forming an integral unit, and an electrical connecting between the electrical contacts of the electronics unit and the contact pads of the sensor. Thus, as discussed above, the body mount may hold the sensor in place, such that the contact pads of the sensor facing away from the body mount, such as facing upwards, towards the electronics unit. During the step of mounting the electronics unit to the body mount, the electrical contacts of the electronics unit may be pressed against the contact pads of the sensor, thereby establishing an electrical connection between the sensor and the electronics unit.

The proposed sensor and the proposed sensor assembly for detecting at least one analyte in a body fluid as well as the proposed methods of manufacturing a sensor and a sensor assembly for detecting at least one analyte in a body fluid provide many advantages over known devices and methods.

The state of the art generally shows sealing concepts which comprise additional components to place a sealing member. In contrast to such concepts, the disclosed invention specifically may relate to a sensor, particularly to the electrochemical sensor, having a sealing ring applied directly to the contact portion of the sensor, particularly to a sensor head, such that the sealing ring may surround the electrical contacts of the sensor. Applying the sealing ring directly to the contact portion of the sensor, particularly to the sensor head, may generally allow of a flat seal with a low construction height. Additionally or alternatively, further connector or sealing elements may be completely or at least partially avoided generally leading to a reduced size of the electrical contacts and/or to a cost reduction due to a reduced number of components.

Exemplary polymers which may provide required properties for sealing may be elastomers, particularly silicone copolymers, particularly Geniomer® materials, based on polysilicone copolymers. Furthermore, the sealing ring may have a sealing lip on the inner perimeter and/or the outer perimeter of the sealing ring which may enhance sealing properties.

The electrical connection between the contact portion of the sensor, particularly the sensor head, and the electronics unit, particularly the transmitter, may be established by pressing the electrical contacts of the electronics unit, particularly the transmitter, e.g. via the pressure element which may particularly be profiled or the housing of the sensor assembly. Placing an elastomer underneath the substrate of the sensor, particularly of the contact portion of the sensor, may generally simplify such contacting.

As outlined above, an additional aspect of the invention relates to a method of manufacturing a sensor, specifically to an electrochemical sensor, with the sealing ring on the contact portion, specifically on the sensor head. In particular, a composition of the sealing material and the application of the sealing material to the contact portion of the sensor, particularly to the sensor head, may influence sealing properties and a formation of the sealing lip.

Further advantages of the disclosed devices and methods may be a low construction height of the sensor assembly, a reduced control expenditure during manufacturing the sensor and/or the sensor assembly as well as a fast integrated manufacturing. Further, a usage of mounting aids and/or holding structures during manufacturing the sensor and/or the sensor assembly may be completely or at least partially reduced. Moreover, each sensor may provide a new sealing ring.

The contact portion may be plane. Still, other embodiments are feasible. The electrical contacts may be surrounded by the sealing ring which may specifically be self-contained. The sealing ring may have a round shape. Still, other shapes are feasible. The sealing ring may have a constant thickness. However, the sealing ring may alternatively show a variation in the thickness. The sealing material may be rigidly connected to the substrate, specifically to the contact portion of the substrate. The sealing material may specifically form a flat seal. Still, other embodiments are feasible. The sealing ring, specifically the flat seal, may be structured in itself. Exemplarily, the sealing ring, specifically the flat seal, may comprise one or more of the sealing lips. The sealing lips may particularly be self-contained.

For manufacturing sealed electrical contacts, the contact portion of the substrate may be pressed onto a counterpart, specifically onto the electronics unit or an arbitrary measurement device, particularly in correct position. For providing a fluid seal a surface of the counterpart, specifically the base of the electronics unit, may show smooth properties and/or may be completely or at least partially free from cracks. The pressing of the contact portion onto the counterpart, specifically onto the electronics unit, specifically onto the electrical contacts of the electronics unit, may be conducted via the pressure element or via an elastomeric element, which may particularly located on a back side of the contact portion of the sensor. The sealing ring, specifically the sealing material may withstand electrolyte solutions containing detergents. A desired press off may be provided by constructional provisions, i.e. by providing the housing, which specifically may surround the sensor at least partially and may be adapted with regard to its size.

For manufacturing the sensor, a ring of the sealing material which may specifically be in a fluid or dissolved state may be applied on the contact portion of the substrate which may specifically be flat. The sealing material may specifically comprise the elastomer, particularly a polymeric elastomer, particularly the thermoplastic elastomer, or a cross-linked polymer. Particularly, the elastomer may be suitable for sterilization, particularly for sterilization via radiation, specifically for meeting the requirements for applying the sensor or the sensor assembly in the medical sector. Therefore, the elastomer specifically may comprise silicones or silicone copolymers.

The sealing material may generally be applied in the fluid state, i.e. as a melt or as a reactive mixture. This may specifically be conducted via injection molding. At least one template may be positioned onto the contact portion and the template may be filled with the melt or the reaction mixture. The melt may harden while cooling down. In case the reactive mixture is applied, a solid sealing may be formed by applying an increased temperature to accelerate a cross-linking reaction. In case of both variants, the template may comprise a structure and the sealing ring may comprise a profile, such as a plurality of cavities.

In case the sealing material is in the dissolved state, the sealing material may be applied via a printing method, such as screen printing or dosing. In case the screen printing is applied, the shape of the sealing ring may at least to a large extend be determined by the screen. However, other printing methods may also be feasible. In case the dosing method is applied, a polymeric solution may exemplarily be deposited via the dosing needle, exemplarily the polymeric solution may be applied in a form of a rope. Particularly, the polymeric solution may be applied as a closed ring on the contact portion of the sensor. A width of the sealing ring may be influenced by a geometry of the contact portion and by the insulating layer. The thickness of the sealing ring may be dependable on a dosing amount of the polymeric solution and by a concentration of the polymeric solution. A surface tension of the fluid may lead to a formation of a smooth surface of the sealing ring. Particularly, the solvent of the sealing material may evaporate at room temperature or by applying an increased temperature. The drying step may be conducted so that a formation of irregularities or wrinkles is completely or at least partially reduced. In case the wrinkles are located on the surface of the sealing ring, an effective sealing may nevertheless be provided, specifically be providing an increased compression.

The applying of the sealing material may depend on the geometry and on further properties of the contact portion of the sensor. Specifically, the insulating layer may have an influence on the formation of the sealing ring. An interface between the electrically insulating material and the substrate may form a flow resistance, specifically for the elastomeric solution. Taking into account the flow resistance, the thickness of the sealing ring may be increased.

Further, bonding agents may optionally be applied to the substrate and/or to the insulating layer, specifically to increase a bonding of the sealing material, specifically of the polymeric sealing material. The bonding agents may be applied in case the sealing material is applied in the dissolved state as well as in case the sealing material is applied in the fluid state.

As outlined above, optionally, a pressure element, which specifically may be an elastomeric pressure element, may be located on the back side of the contact portion of the substrate. The pressure element may have a larger thickness than the sealing ring, exemplarily 1 mm. For applying the pressure element, several methods may be used. The pressure element may be transferred to the back site of the contact portion adhesive bonding, for example by wetting the pressure element with a solvent and subsequent proof or by utilizing adhesive materials. Additionally, the pressure element may be applied onto a surface, specifically onto the base of the body mount, by injection molding. The bonding agents may also be applied during injecting molding, for example the bonding agents may be distributed within the thermoplastic elastomer of the pressure element.

Summarizing the findings of the present invention, the following embodiments are preferred:

Embodiment 1

A sensor for detecting at least one analyte in a body fluid, specifically for use as a transcutaneous sensor, the sensor having at least one substrate, the sensor further having at least two electrodes applied to the substrate, the electrodes being adapted for detecting the analyte, the sensor further having at least two contact pads applied to the substrate and at least two electrical traces applied to the substrate, the electrical traces electrically connecting the electrodes and the contact pads, wherein the sensor further comprises a sealing ring fixedly applied to the substrate, the sealing ring surrounding the contact pads.

Embodiment 2

The sensor according to the preceding embodiment, wherein the contact pads are commonly located as a group on a surface of the substrate, wherein the sealing ring commonly surrounds the group.

Embodiment 3

The sensor according to any one of the preceding embodiments, wherein the sealing ring has a constant thickness, specifically a constant maximum height along a sealing line defined by the sealing ring.

Embodiment 4

The sensor according to any one of the preceding embodiments, wherein the sealing ring is fixedly connected to the substrate by material engagement.

Embodiment 5

The sensor according to any one of the preceding embodiments, wherein the sealing ring comprises at least one polymer.

Embodiment 6

The sensor according to any one of the preceding embodiments, wherein the sealing ring comprises at least one elastomer.

Embodiment 7

The sensor according to the preceding embodiment, wherein the elastomer comprises at least one silicone material, preferably at least one silicone and/or a silicone polymer.

Embodiment 8

The sensor according to any one of the two preceding embodiments, wherein the elastomer comprises at least one silicone copolymer, such as a copolymer of polydimethylsiloxane, such as a copolymer of polydimethylsiloxane and urea, such as a poly(dimethylsiloxane)polyurea copolymer.

Embodiment 9

The sensor according to any one of the three preceding embodiments, wherein the elastomer comprises at least one polyurea copolymer.

Embodiment 10

The sensor according to any one of the four preceding embodiments, wherein the elastomeric is a thermoplastic elastomer or a cured elastomer.

Embodiment 11

The sensor according to any one of the preceding embodiments, wherein the sealing ring comprises at least one sealing lip.

Embodiment 12

The sensor according to the preceding embodiment, wherein the sealing lip is located on one or both of an inner or outer perimeter of the sealing ring.

Embodiment 13

The sensor according to any one of the two preceding embodiments, wherein the sealing lip is spaced apart from the substrate.

Embodiment 14

The sensor according to any one of the preceding embodiments, wherein the sealing ring has a shape selected from the group consisting of: a circular shape, an oval shape, a polygon shape, a rectangular shape, an arbitrary shape.

Embodiment 15

The sensor according to any one of the preceding embodiments, wherein the sensor further comprises at least one electrically insulating material, preferably an insulating resist, the electrically insulating material at least partially covering the electrical traces, the insulating material leaving open the electrodes and the contact pads.

Embodiment 16

The sensor according to the preceding embodiment, wherein the electrically insulating material comprises at least one insulating cover layer covering the electrical traces.

Embodiment 17

The sensor according to any one of the two preceding embodiments, wherein the electrically insulating material forms openings, wherein the electrodes are located within the openings.

Embodiment 18

The sensor according to any one of the three preceding embodiments, wherein the substrate comprises at least one contact portion to be connected to at least one control part of a sensor assembly comprising the sensor, specifically to a body mount of the control part, wherein, in the contact portion, the contact pads are located, wherein the electrically insulating material at least not fully covers the contact portion.

Embodiment 19

The sensor according to any one of the four preceding embodiments, wherein the electrically insulating material is distinct from the sealing ring.

Embodiment 20

The sensor according to any one of the five preceding embodiments, wherein the sealing ring exceeds the electrically insulating material, specifically at least one insulating layer formed by the electrically insulating material, in height, preferably by at least a factor of 1.5, more preferably by at least a factor of 2.

Embodiment 21

The sensor according to any one of the six preceding embodiments, wherein the sealing ring fully or partially is applied onto the insulating material.

Embodiment 22

The sensor according to any one of the preceding embodiments, wherein the sealing ring is directly applied to the substrate.

Embodiment 23

The sensor according to any one of the preceding embodiments, wherein the sealing ring is producible by applying a liquid or pasty sealing material to the substrate.

Embodiment 24

The sensor according to the preceding embodiment, wherein the liquid or pasty sealing material is fully or partially hardened after application.

Embodiment 25

The sensor according to any one of the preceding embodiments, wherein the at least two electrodes comprise at least one working electrode having at least one test chemical being sensitive to the analyte to be detected.

Embodiment 26

The sensor according to the preceding embodiment, wherein the working electrode further comprises at least one conductive working electrode pad, wherein the conductive working electrode pad is in contact with the at least one test chemical.

Embodiment 27

The sensor according to any one of the preceding embodiments, wherein the at least two electrodes comprise at least one counter electrode.

Embodiment 28

The sensor according to any one of the preceding embodiments, wherein the at least two electrodes further comprise at least one reference electrode.

Embodiment 29

The sensor according to any one of the two preceding embodiments, wherein the counter electrode and the reference electrode are one of a common electrode or two separate electrodes.

Embodiment 30

The sensor according to any one of the preceding embodiments, wherein the substrate is a flexible substrate, preferably a substrate comprising at least one foil, more preferably a substrate comprising at least one polyimide foil.

Embodiment 31

The sensor according to any one of the preceding embodiments, wherein the substrate is an elongate substrate, with the electrodes being placed at one end of the elongate substrate and the contact pads being placed on an opposing end of the substrate.

Embodiment 32

The sensor according to any one of the preceding embodiments, wherein the substrate comprises at least one contact portion, wherein the contact pads are located in the contact portion.

Embodiment 33

The sensor according to the preceding embodiment, wherein the contact portion is widened as compared to the remaining substrate.

Embodiment 34

The sensor according to any one of the two preceding embodiments, wherein the contact portion is a rectangular contact portion.

Embodiment 35

A sensor assembly for detecting at least one analyte in a body fluid, the sensor assembly comprising at least one sensor according to any one of the preceding embodiments, the sensor assembly further comprising at least one control part having at least one electronics unit component for one or more of controlling the detection of the analyte or transmitting measurement data to another component, wherein the control part, preferably the electronics unit of the control part, comprises at least two electrical contacts, wherein the electrical contacts are electrically connected to the contact pads of the sensor.

Embodiment 36

The sensor assembly according to the preceding embodiment, wherein the electrical contacts of the control part directly contact the contact pads of the sensor.

Embodiment 37

The sensor assembly according to any one of the two preceding embodiments, wherein the sensor assembly further comprises at least one pressure element configured for pressing the contact pads of the sensor onto the electrical contacts of the control part or vice versa.

Embodiment 38

The sensor assembly according to the preceding embodiment, wherein the pressure element is part of the control part, specifically of the body mount.

Embodiment 39

The sensor assembly according to any one of the two preceding embodiments, wherein the pressure element is one of both of flexible or deformable.

Embodiment 40

The sensor assembly according to any one of the preceding embodiments referring to a sensor assembly, wherein the control part comprises a body mount having a surface mountable to a skin of a user.

Embodiment 41

The sensor assembly according to any one of the preceding embodiments referring to a sensor assembly, wherein the control part comprises at least one housing.

Embodiment 42

A method of manufacturing a sensor for detecting at least one analyte in a body fluid, preferably a sensor according to any one of the preceding embodiments referring to a sensor, the method comprising the following steps:
  providing at least one substrate;
  applying at least two electrodes to the substrate;
  applying at least two contact pads to the substrate;
  applying at least two electrical traces to the substrate, the electrical traces interconnecting the contact pads and the electrodes; and applying at least one sealing ring fixedly to the substrate, wherein the sealing ring surrounds the contact pads.

Embodiment 43

The method according to the preceding embodiment, wherein the step of applying the at least one sealing ring fixedly to the substrate comprises at least one application method selected from the group consisting of: a printing method, such as a printing method selected from the group consisting of a screen printing, a stencil printing, an inkjet printing or an offset printing; a dosing method using at least one dosing head, such as a dosing needle and/or a dispenser.

Embodiment 44

The method according to the two preceding embodiments, wherein the step of applying the at least one sealing ring comprises applying at least one sealing material to the substrate in a patterned fashion.

Embodiment 45

The method according to the three preceding embodiments, wherein the step of applying the at least one sealing ring fixedly to the substrate comprises applying at least one sealing material, such as in a liquid or pasty form, to the substrate.

Embodiment 46

The method according to the preceding embodiment, wherein the step of applying the at least one sealing ring fixedly to the substrate further comprises at least one curing step, wherein in the curing step the sealing material is fully or partially hardened.

Embodiment 47

The method according to the preceding embodiment, wherein the curing step comprises at least one of: a thermal curing, preferably one or both of a cooling or heating; a curing by evaporating at least one solvent, preferably by the using a vacuum; a photo curing; a chemical curing.

Embodiment 48

The method according to the two preceding embodiments, wherein the curing step comprises one or more of a hardening by cooling of the sealing material or a curing by chemical cross-linking of the sealing material.

Embodiment 49

The method according to the four preceding embodiments, wherein the sealing material comprises at least one solvent.

Embodiment 50

The method according to the five preceding embodiments, wherein the sealing material comprises at least one of a polymer material, a plastic material or a precursor material capable of cross-linking and/or polymerizing.

Embodiment 51

The method according to the six preceding embodiments, wherein the sealing material comprises a solution of at least one matrix material in at least one solvent.

Embodiment 52

A method of manufacturing a sensor assembly for detecting at least one analyte in a body fluid, specifically a sensor assembly according to any one of the preceding embodiments referring to a sensor assembly, the method comprising the following steps
  providing a sensor for detecting the at least one analyte in the body fluid, the sensor having at least one substrate, the sensor further having at least two electrodes applied to the substrate, the electrodes being adapted for detecting the analyte, the sensor further having at least two contact pads applied to the substrate and at least two electrical traces applied to the substrate, the electrical traces electrically connecting the electrodes and the contact pads, wherein the sensor further comprises a sealing ring fixedly applied to the substrate, the sealing ring surrounding the contact pads;
  providing at least one control part, specifically a control part having at least one electronics unit having at least one electronic component for one or more of controlling the detection of the analyte or transmitting measurement data to another component, wherein the control part comprises at least two electrical contacts; and
  electrically connecting the electrical contacts to the contact pads of the sensor.

Embodiment 53

The method according to the preceding embodiment, wherein the step of electrically connecting the electrical contacts of the control part to the contact pads of the sensor implies pressing the contact pads of the sensor onto the electrical contacts of the control part or vice versa.

Embodiment 54

The method according to any one of the two preceding embodiments, wherein the control part comprises at least one body mount having a surface mountable to a skin of a user and at least one electronics unit for one or more of controlling the detection of the analyte or transmitting measurement data to another component, the electronics unit having the electrical contacts of the control part, wherein the step of electrically connecting the electrical contacts of the control part to the contact pads of the sensor comprises the following sub-steps:
  mounting the sensor to the body mount such that contact pads of the sensor are facing away from the body mount;
  mounting the electronics unit to the body mount such that the electrical contacts of the electronics unit are pressed against contact pads of the sensor or vice versa.

SHORT DESCRIPTION OF THE FIGURES

Further optional features and embodiments of the invention will be disclosed in more detail in the subsequent description of preferred embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

In the Figures

Figure 3:
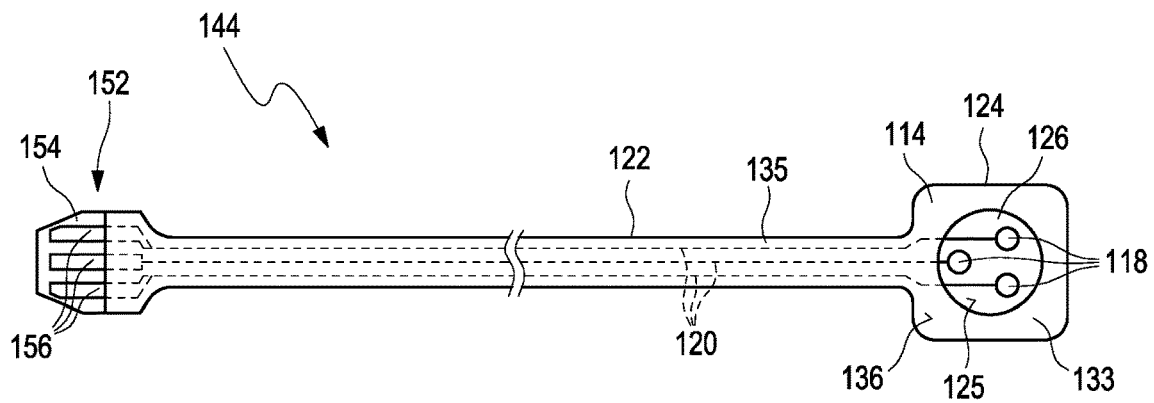
Figure 3:
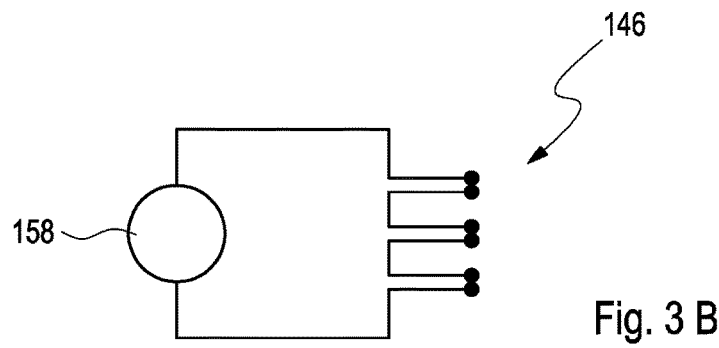
Figure 3:
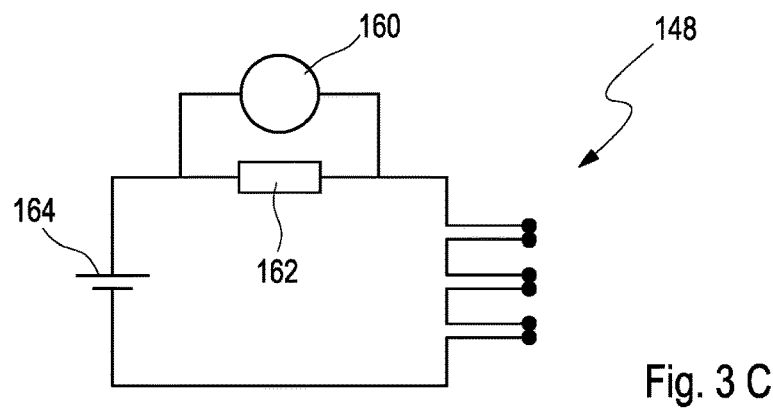
Figure 3:
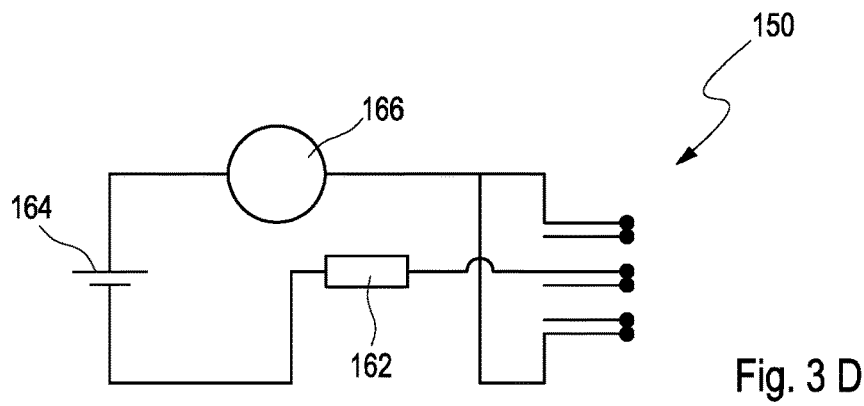
Figure 4:
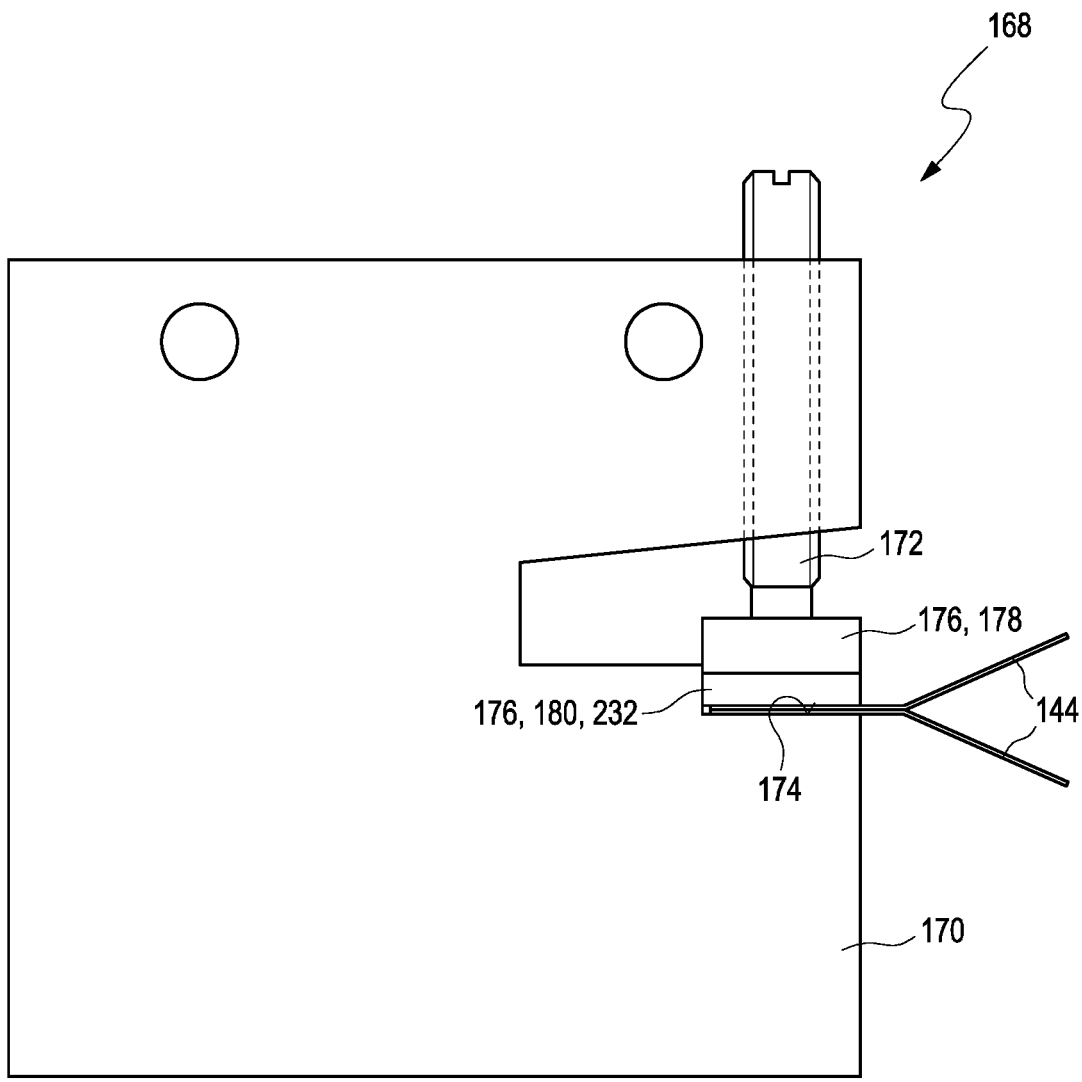
Figure 4:
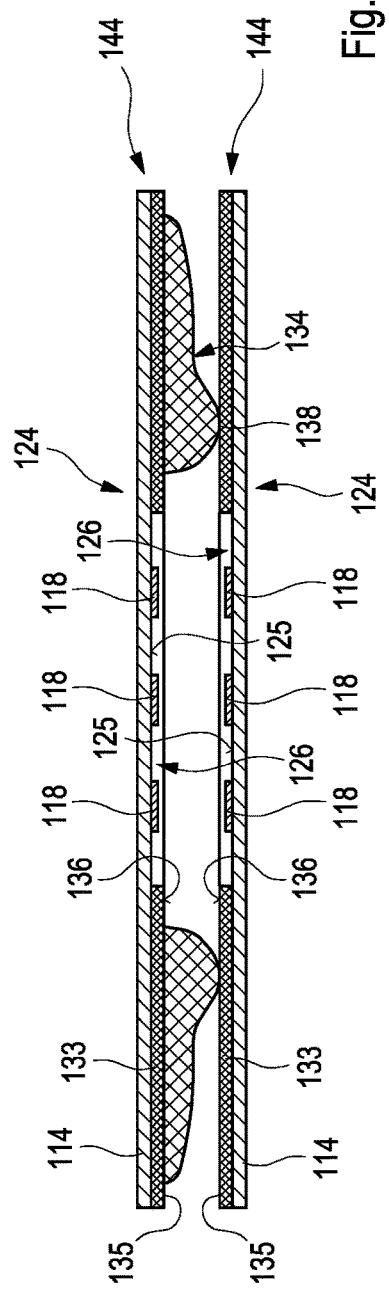
Figure 4:
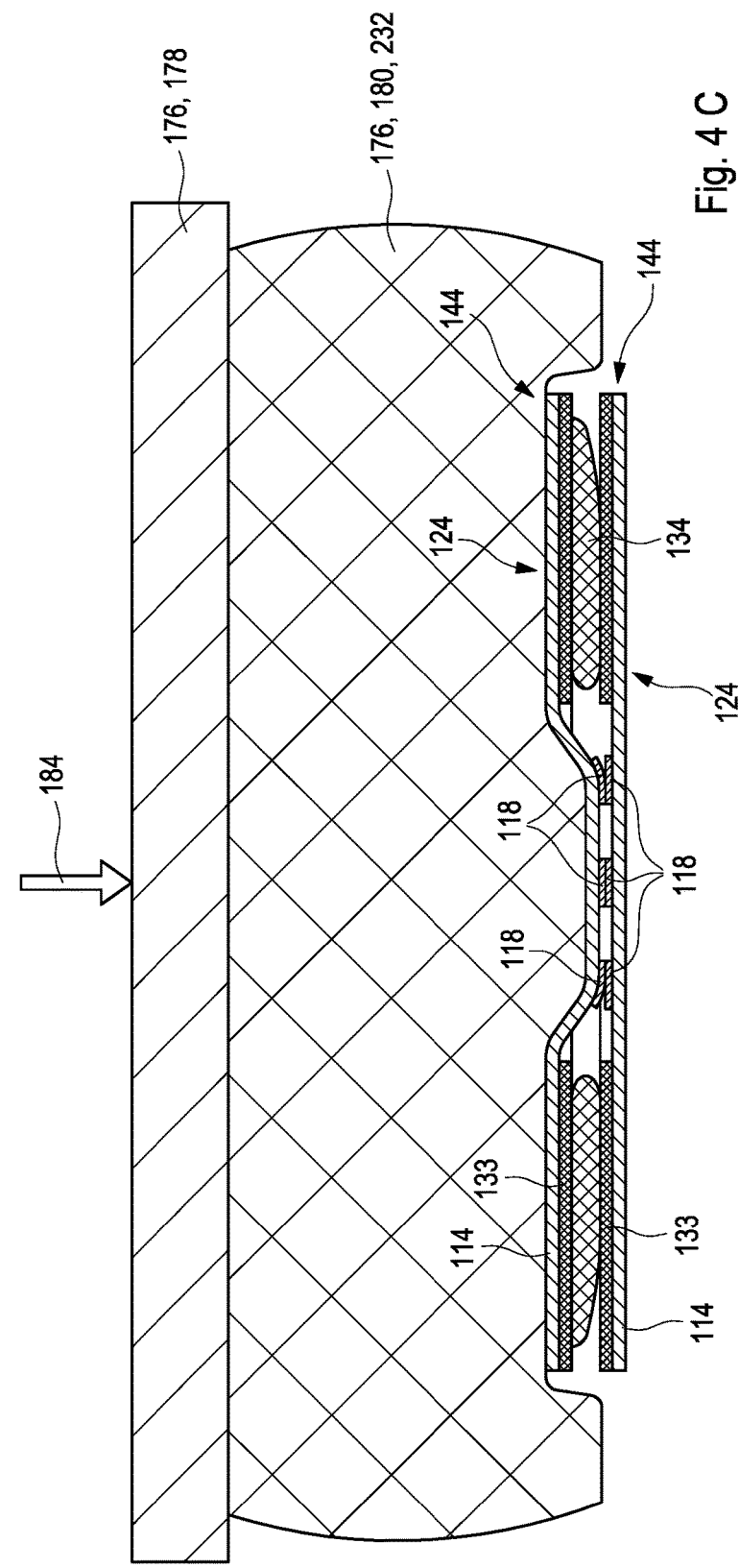
Figure 5:
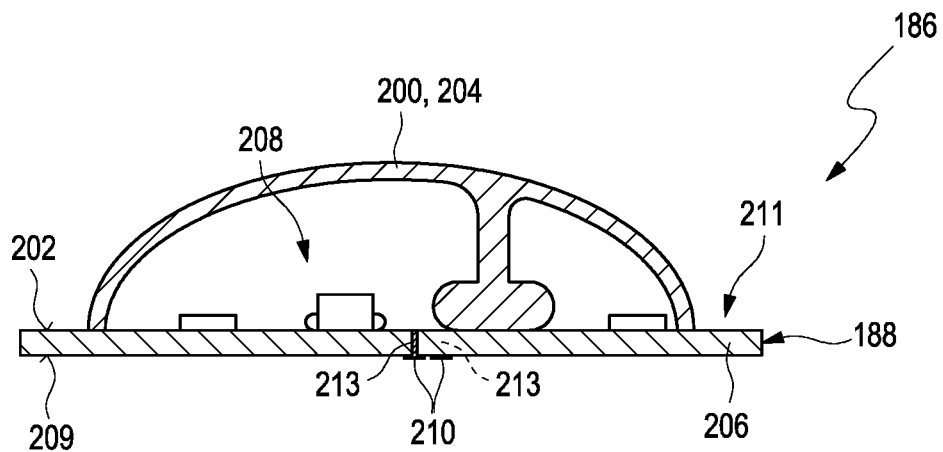
Figure 5:
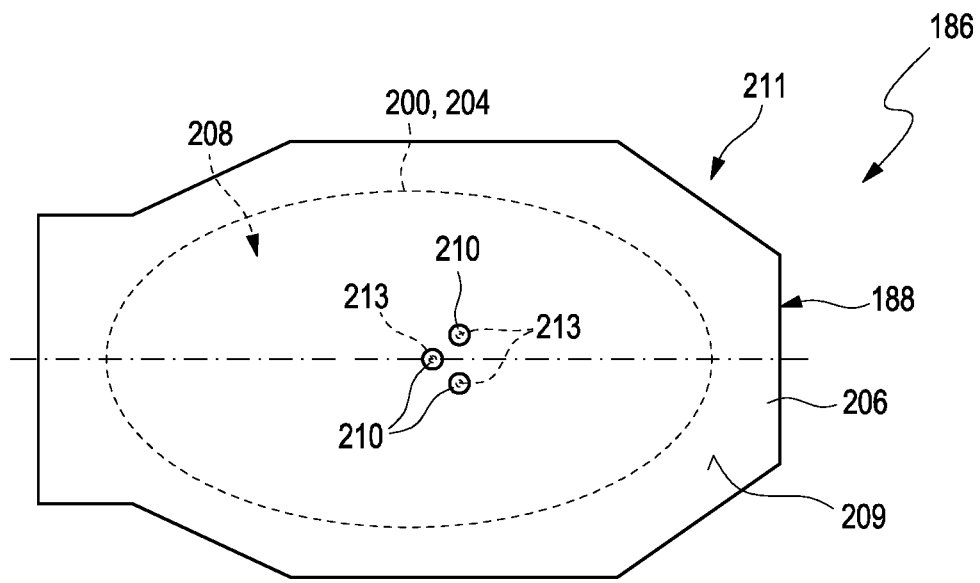
Figure 6:
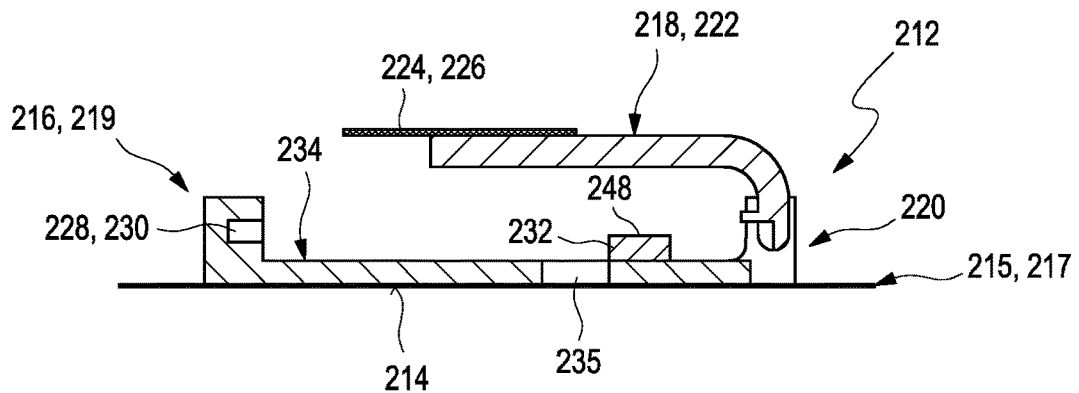
Figure 6:
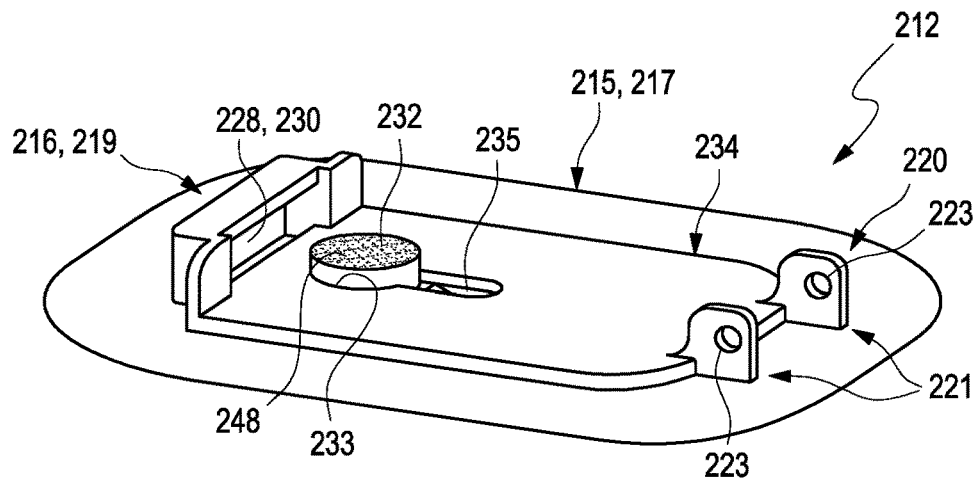
Figure 6:
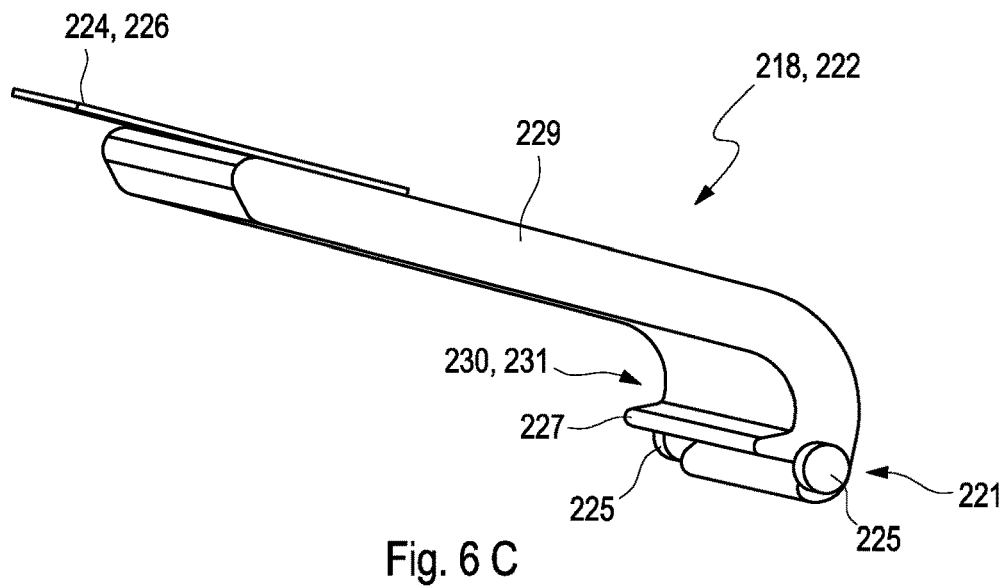
Figure 7:
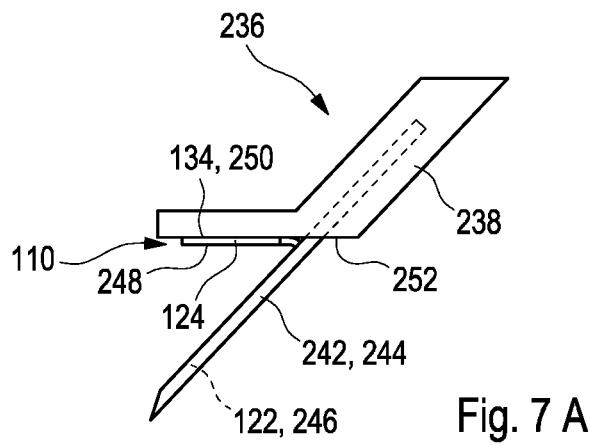
Figure 7:
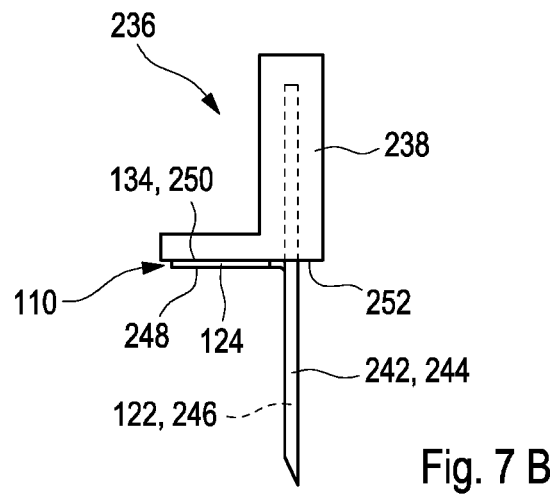
Figure 7:
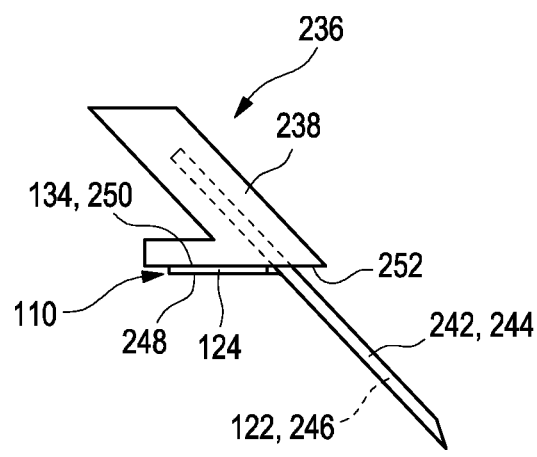
Figure 8:
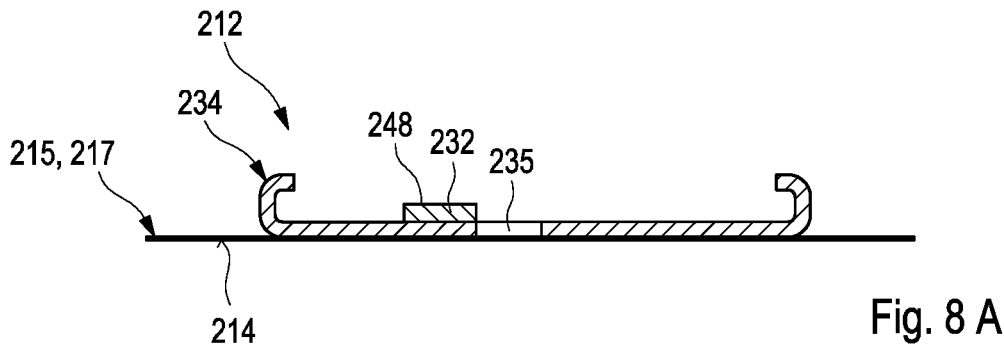
Figure 8:
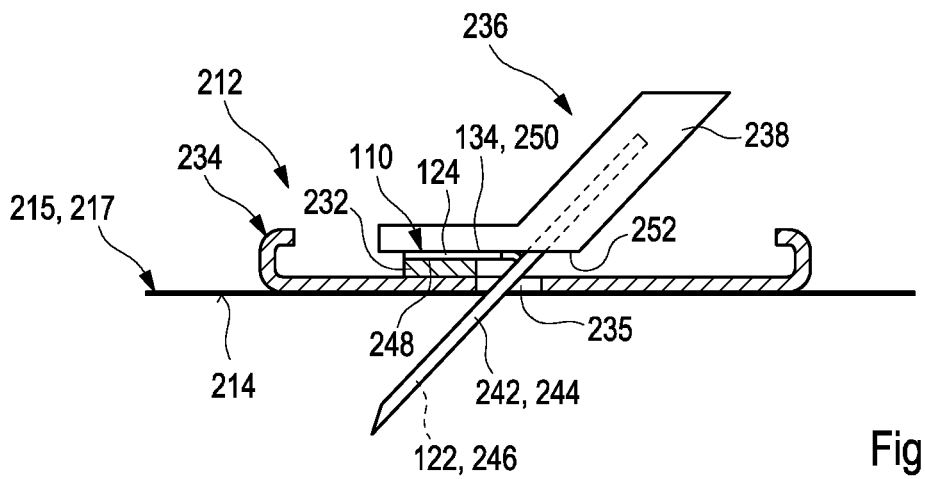
Figure 8:
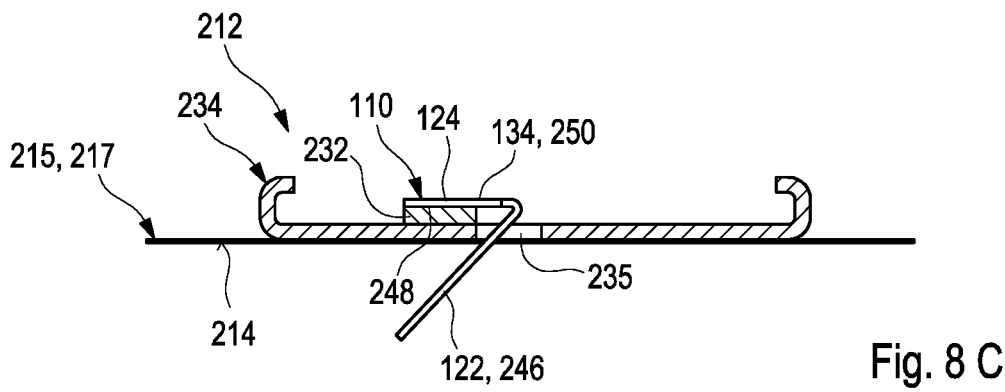
Figure 8:
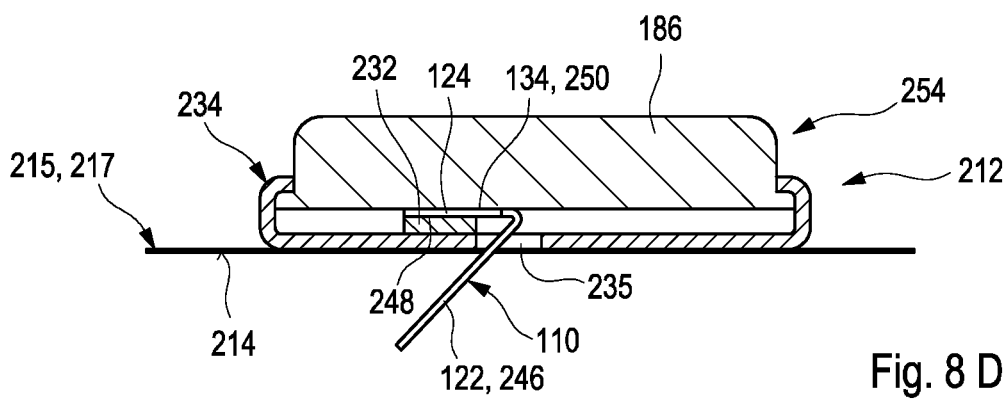
Figure 9:
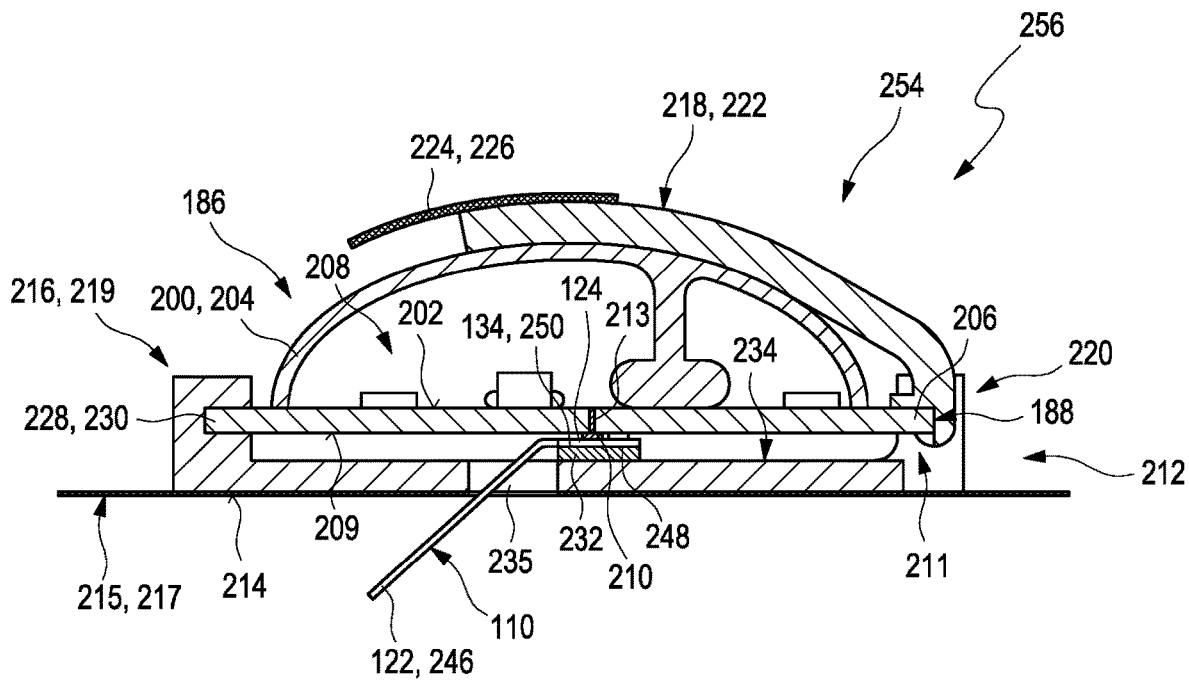
Figure 9:
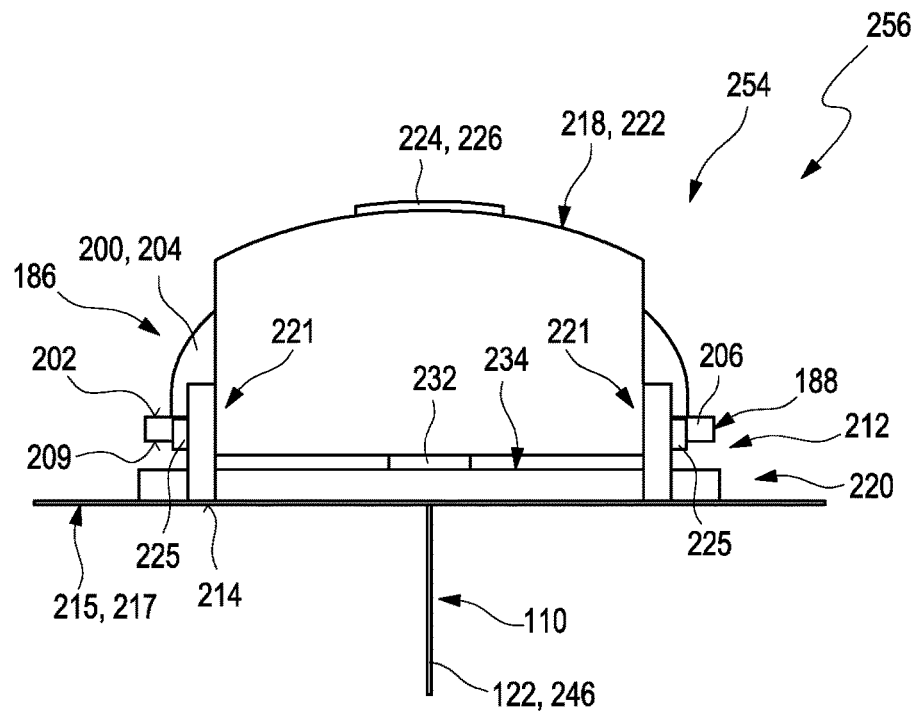
Figure 10:
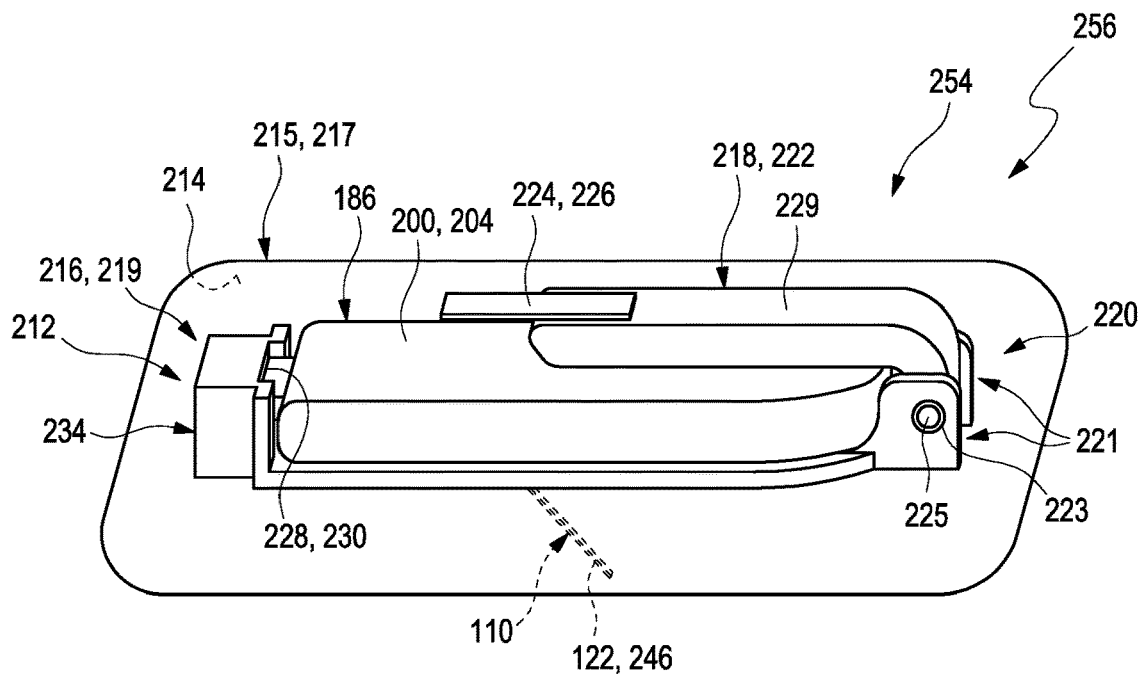
Figure 10:
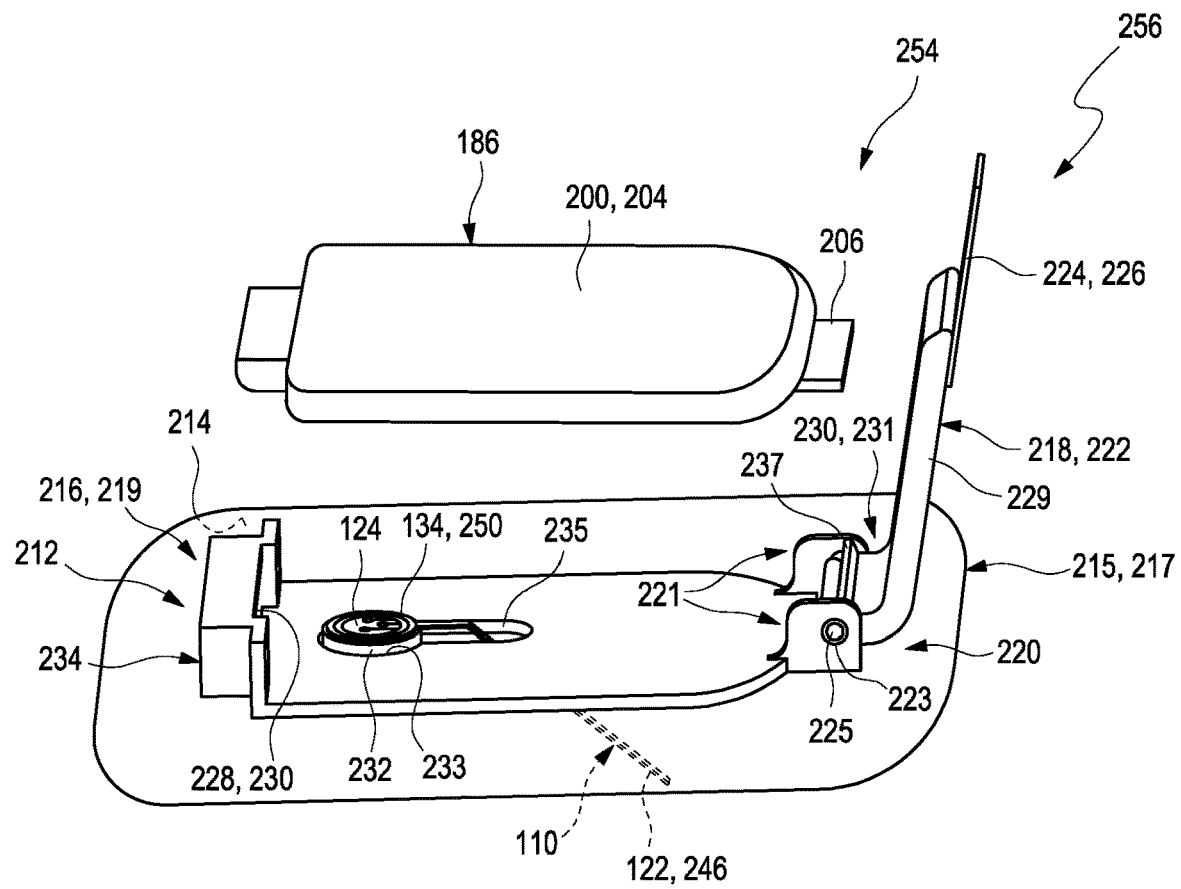

FIGS. 3A to 3D show various components of an exemplary testing setup for testing the sealing performance of the sealing ring, including a dummy test element for simulating a sensor (FIG. 3A), a first circuit diagram of an electrical setup for measuring an electrical resistance of the contact pads (FIG. 3B), a second circuit diagram of an electrical setup for measuring a vibration resistance (FIG. 3C) and a third circuit diagram of an electrical setup for measuring an insulation resistance (FIG. 3D);

FIGS. 4A to 4C show an exemplary testing setup for testing a sealing ring (FIG. 4A) and schematic representations of an electrical connection between contact pads of a sensor and electrical contacts of an electronics unit without applying pressure (FIG. 4B) and with applying pressure by using a pressure element (FIG. 4C);

FIGS. 5A to 5B show an exemplary embodiment of an electronics unit of a sensor assembly in a cross-sectional view (FIG. 5A) and in a bottom view (FIG. 5B);

FIGS. 6A to 6C show components of an exemplary embodiment of a body mount of a control part of a sensor assembly;

FIGS. 7A to 7C show different embodiments of an insertion element;

FIGS. 8A to 8D show a method of mounting a sensor to a body mount;

FIGS. 9A to 9B show an exemplary embodiment of a sensor assembly in a cross-sectional view (FIG. 9A) and in a side view (FIG. 9B); and FIGS. 10A to 10B show an exemplary embodiment of a sensor assembly in a perspective view in a fully assembled state (FIG. 10A) and in a disassembled state (FIG. 10B).

DETAILED DESCRIPTION OF THE EMBODIMENTS

Figure 1:
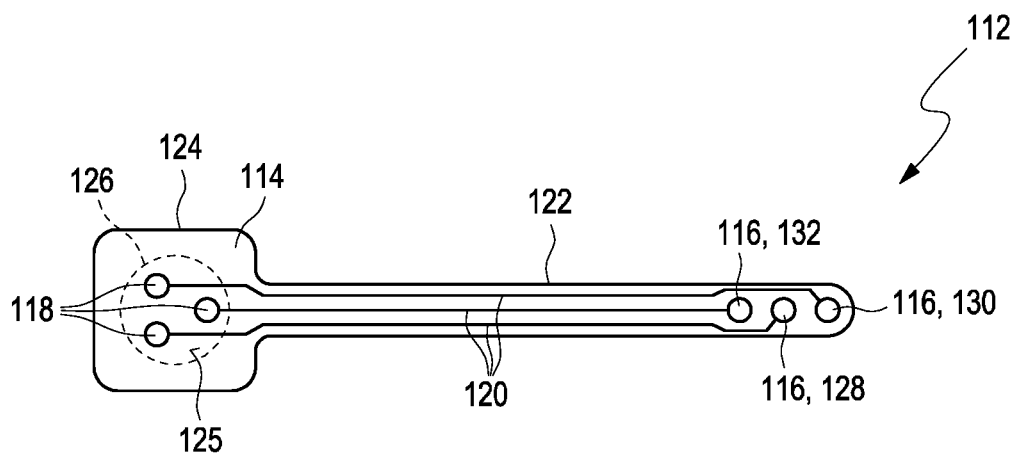
FIGS. 1A and 1B show an exemplary embodiment of a sensor for detecting at least one analyte in a body fluid and of a method of manufacturing the same.
Figure 1:
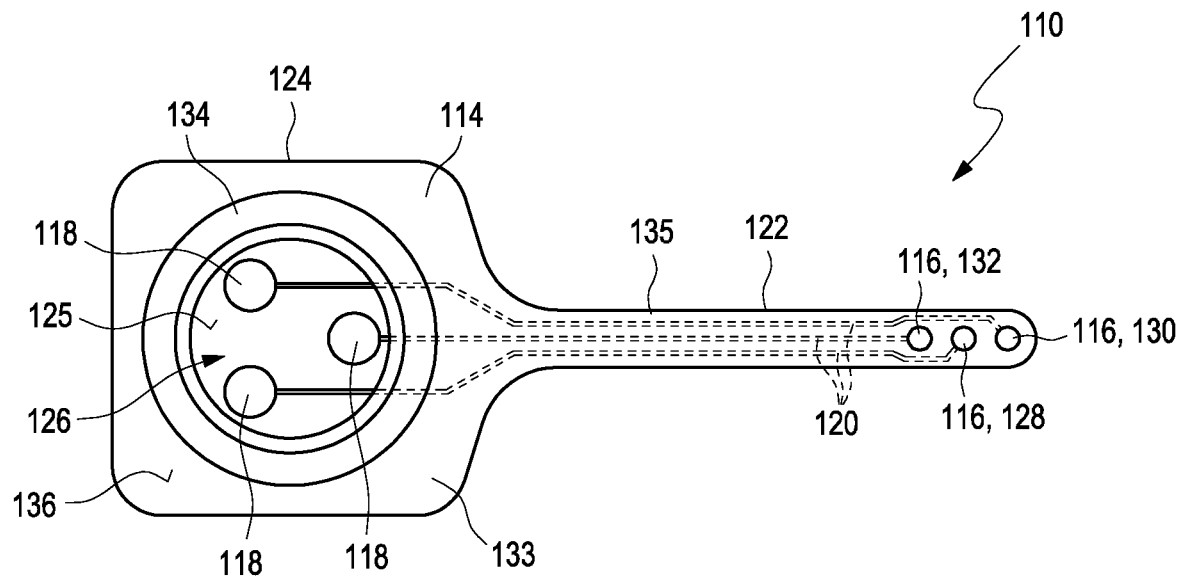

In FIGS. 1A and 1B, an exemplary embodiment of a sensor 110 for detecting at least one analyte in a body fluid and of a method of manufacturing the same are shown. FIG. 1A shows an intermediate product 112 of the sensor 110, whereas the sensor 110 is illustrated in FIG. 1B. However, other embodiments of the sensor 110 are feasible.

In a first step, as shown in FIG. 1A, at least one substrate 114 may be provided, at least two electrodes 116 may be applied to the substrate 114, at least two contact pads 118 may be applied to the substrate 114 and at least two electrical traces 120 may be applied to the substrate 114. For potential techniques for application of these elements 116, 118 and 120, reference may be made to the disclosure above and/or to conventional techniques used for manufacturing circuit boards, specifically flexible circuit boards. Elements 116, 118 and 120 may fully or partially be applied in a single step or in separate steps. Various embodiments are feasible, as the skilled person will recognize.

The substrate 114, which specifically may be or may comprise a flexible substrate such as a flexible foil, specifically may comprise a shaft 122 and a contact portion 124. The shaft 122 may have an elongate shape. The contact portion 124 may be widened as compared to the remaining substrate 114. As an example, the contact portion 124 may be a rectangular contact portion 124. The substrate 114 may be a flexible substrate 114. For example, the substrate 114 may comprise at least one polyimide foil.

The electrical traces 120 preferably may have an elongated shape. Further, the electrical traces 120 may fully or partially be located on the shaft 122 of the substrate 114. The electrical traces 120 may electrically interconnect the contact pads 118 and the electrodes 116. The electrical traces 120 may comprise at least one electrically conductive material. Exemplarily, the electrical traces 120 may comprise copper. However, other embodiments are feasible, as outlined in further detail above.

The contact pads 118 may be located inside a contact surface area 126, which may be a surface area covering the contact pads 118. In FIG. 1A the contact surface area 126 is symbolically depicted by a dashed circle. Particularly, the contact surface area 126 may have a circular and/or rectangular shape.

The contact pads 118, as outlined above, may be fully or at least partially made of a metallic material. Specifically, the contact pads 118 may comprise at least one gold layer. The contact pads 118 may be located in the contact portion 124.

The electrodes 116 may comprise at least one working electrode 128 adapted for performing at least one electrochemical detection reaction for detecting the at least one analyte in the body fluid. The working electrode 128 may have at least one test chemical being sensitive to the analyte to be detected. As an example, the at least one test chemical may be deposited on top of a working electrode pad which has electrically conductive properties. Further, the electrodes 116 may comprise at least one counter electrode 130 adapted for performing at least one electrochemical counter reaction adapted for balancing a current flow required by the detection reaction at the working electrode 128. Additionally, the electrodes 116 may further comprise at least one reference electrode 132 which may have a stable and well-known electrode potential. It shall be noted, however, that other electrode setups may be feasible, such as setups having more than three electrodes or less than three electrodes, such as by combining the counter electrode 130 and the reference electrode 132. It also may be feasible to have at least one of the electrodes 116, at least one of the electrical traces 120 and at least two of the contact pads 118 applied to a first side of the substrate 114 and have at least one of the electrodes 116 and at least one of the electrical traces 120 applied to a second side of the substrate 114 and connected with at least one contact pad 118 on the first side by at least one via. Thus, generally, a more complex geometry or a more complex layer setup of the sensor 110 is generally feasible, such as a layer setup having electrical traces 120 in different planes of the layer setup and, as an example, using contact pads 118 on different sides and/or using vias for providing electrical contact between one or more of the contact pads 118 and one or more of the electrical traces 120.

In a second step, as illustrated in FIG. 1B, at least one electrically insulating material 133 may be applied to the substrate 114. In case at least one insulating material 133 may be applied to the substrate 114, the electrically insulating material 133 itself, after application, may form part of the substrate 114. Thus, in the context of the present invention, when reference is made to applying one or more elements to the substrate 114, the one or more elements may directly be applied to the substrate 114 or may be applied to the substrate 114 with the insulating material 133 disposed thereon.

For example, the electrically insulating material 133 may comprise an insulating resist. However, other materials are feasible. The electrically insulating material 133 may at least partially cover the electrical traces 120, the electrically insulating material 133 leaving open the electrodes 116 and the contact pads 118. Particularly, the electrically insulating material 133 may comprise at least one insulating cover layer 135 covering the electrical traces 120.

Further, at least one sealing ring 134 may be applied fixedly to the substrate 114. The sealing ring 134 may be fully or partially applied onto the electrically insulating material 133. The sealing ring 134 may exceed the electrically insulating material 133 in height. Particularly at least one insulating layer 136 may be formed by the electrically insulating material 133.

The step of applying the sealing ring 134 may comprise applying at least one sealing material, preferably in a liquid or pasty form, to the substrate 114. The contact pads 118 may be commonly located as a group on a surface 125 of the substrate 114 and the sealing 134 may commonly surround the group. The sealing material may specifically comprise at least one solvent and may further comprise at least one matrix material, such as one of a polymer material, a plastic material or a precursor material capable of cross-linking or polymerizing. The step of applying the sealing ring 134 may comprise at least one application method, such as a dosing method, e.g. a dispensing method. Further, the step of applying the at least one sealing ring 134 may comprise at least one curing step. Consequently, in the curing step, the sealing material may be fully or partially hardened.

The substrate 114 was manufactured by utilizing a polyimide foil with a thickness of 50 µm from Contag AG, Berlin, Germany. The contact portion 124 of the substrate 114 had dimensions of 5 mm×5 mm. The electrical traces 120 were made of copper. Additionally, the electrical traces 120 were galvanized with gold plating. The contact pads 118 and the electrodes 116 were also galvanized with gold plating. The electrical traces 120, the contact pads 118 and the electrodes 116 had an average thickness of 18 µm respectively. The contact pads 118 had an average diameter of 0.6 mm. The electrical traces 120 and the substrate 114 were isolated via the insulating layer 136, which had an average thickness of about 28 µm. The contact surface area 126 had an average diameter of 2.4 mm.

The sealing material was manufactured as follows: 4.357 g of Geniomer® 145 from Wacker Chemie AG were dissolved in 13.43 g of isopropyl alcohol at 80° C. while stirring for 8 hours. After that, the sealing material was filtered by using a syringe filter with an average pore size of 5.0 µm from Whatman, GE-Healthcare UK Limited, Little Chalfont, UK. A slightly turbid solution was received.

The sealing material was put into a 1 ml syringe and the sealing material was deposited onto the contact portion 124 of the substrate 114 as a closed ring via a dosing needle Tip 23 GA.013X.5 Orange 50 PC from GLT, Pforzheim, Germany. The sealing material was dried at 80° C. for 2 hours. After drying, the sealing ring 134 had an average thickness of around 45 µm.

Figure 2:
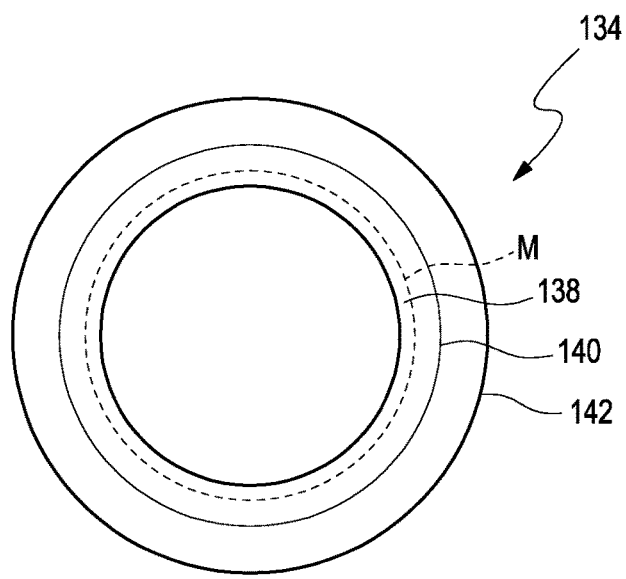
FIGS. 2A to 2C show an exemplary embodiment of a sealing ring in a top view (FIG. 2A) and in a cross-sectional view (FIG. 2B), and a height profile measurement of the sealing ring (FIG. 2C)
Figure 2:
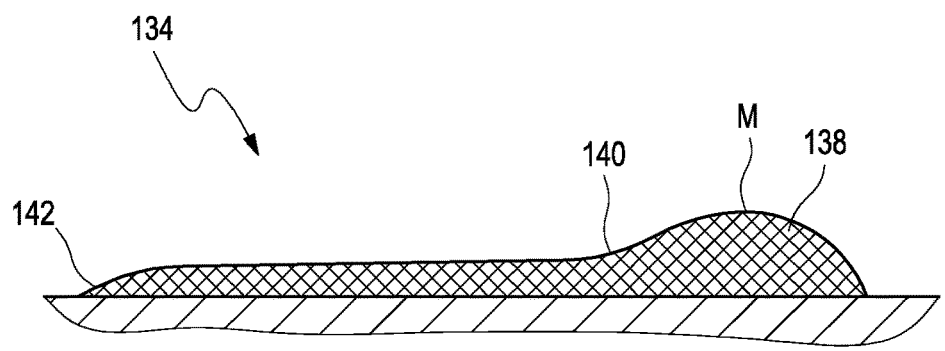
Figure 2:
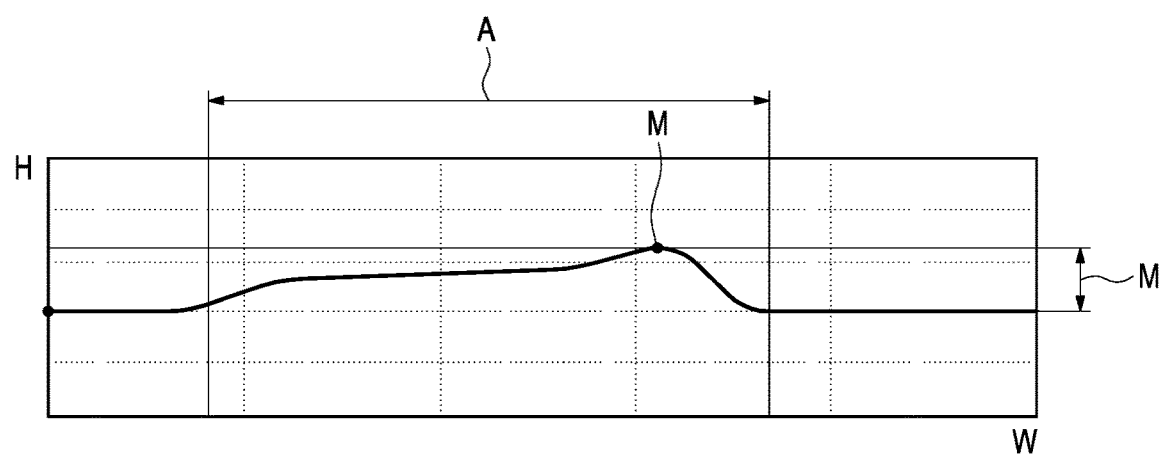

FIGS. 2A to 2C show details of an exemplary embodiment of the sealing ring 134 in various views. Thus, FIG. 2A shows a top view. FIG. 2B shows a cross-sectional view in a plane perpendicular to a surface of the substrate 114 of the sensor 110, oriented radially in the sealing ring 134. FIG. 2C shows a high-profile measurement of the sealing ring 134, also in the plane of the cross-sectional view of FIG. 2B.

The sealing ring 134 as depicted in FIGS. 2A and 2B exemplarily may be manufactured by the method as described above, such as by dispensing. The sealing ring 134 may have a circular shape. Specifically, the sealing ring 134 may have a constant thickness over its circumference. Thus, as depicted in FIGS. 2A to 2C, the points M of maximum height 134 may form a circular or noncircular closed sealing line, which is denoted symbolically by the dashed circle M in FIG. 2A. Along this sealing line, the sealing ring 134 may have a constant thickness. It shall be noted, however, that other embodiments are feasible. Furthermore, the sealing ring 134 may comprise at least one sealing lip 138, which is formed by the local maximum M in the height profile, as seen in FIGS. 2B and 2C. In this embodiment, the sealing lip 138 may be located closer to the inner perimeter 140 of the sealing ring 134 then to the outer perimeter. Thus, the profile of the sealing ring 134 generally may be asymmetrical. Alternatively, however, other profiles are feasible, such as symmetrical profiles or profiles with the sealing lip 138 being located on the outer perimeter 142 of the sealing ring 134.

The sealing ring 134 may comprise at least one silicone material such as an elastomeric silicone material. Particularly, the sealing ring 134 may be designed to be compressed during assembly between two or more elements.

In experiments, 30% to 50% solutions of Geniomer® (Geniomer® 145 or Geniomer® 345) from Wacker Chemie AG, Munich, Germany, dissolved in isopropyl alcohol were deposited onto the substrate 114 via a dosing method. The substrate 114 was manufactured by utilizing a polyimide foil. Further, the substrate 114 comprised the insulating layer 136. As dosing needles Tip 27 GA GP0.008×0.25 CLEAR and Tip 25 GA GP0.010×0.25 RED from Nordson EDF, Westlake, Ohio, USA, with an outer diameter of 0.4 mm or 0.5 mm respectively and an inner diameter of 0.203 mm or 0.254 mm respectively were applied. The dosing pressure was 2.0 bar to 4.0 bar and the velocity of the dosing needles was 2.6 mm/s to 5.0 mm/s. The diameter of application was 3.0 mm. One or two circulations of the dosing needles were conducted. The sealing ring 134 had a round shape and comprised the sealing lip 138 with a height ranging from 55 µm to 170 µm. Generally, the height of the sealing lip 138 increased with the volume of the dosed sealing material.

Further, when the sealing material was deposited along a straight line, it was found that after the curing step the sealing comprised two sealing lips 138 located on both sides of the sealing. Consequently, the sealing material generally behaves according to the so called coffee-ring or coffee-stain effect. Generally, the coffee-ring or coffee-stain effect may also be observed in case a spherical shaped drop of a 25% solution of Geniomer® 145 dissolved in isopropyl alcohol with a diameter of around 3.5 mm is dried. In this case, however, a distinctive bead close to a rim of the drop was observed. In contrast, a drop which is deposited as a thin layer may generally dry without forming a distinctive bead. Therefore, surprisingly, it was found that a sealing lip 138 located on the inner perimeter 140 of the sealing ring 134 was formed by applying the elastomeric solution as sealing material.

In FIG. 2C an exemplary embodiment of potential dimensions of the sealing ring 134 is shown. Therein, a horizontal axis, denoted by W, is an axis which radially extends with respect to the sealing ring 134, parallel to a surface of the substrate 114. The vertical axis in FIG. 2C, denoted by H, shows the local height of the sealing ring 134. As can be seen in this high profile, in this embodiment, the width A of the sealing ring 134 may be in the range of e.g. 400 μm to 700 μm, such as 560 μm, and the maximum height M may be in the range from 50 μm to 80 μm, preferably 65 μm. However, other dimensions are generally feasible.

FIGS. 3A to 3D show various components of an exemplary testing setup for testing the sealing performance of the sealing ring 134. The testing setup specifically may comprise an exemplary test element 144, also referred to as a dummy test element or a dummy sensor, (FIG. 3A), an electrical setup according to a first circuit diagram 146 for measuring an electrical resistance of the contact pads 118 (FIG. 3B), an electrical setup according to a second circuit diagram 148 for measuring a vibration resistance (FIG. 3C) and an electrical setup according to a third circuit diagram 150 for measuring an insulation resistance (FIG. 3D).

The test element 144 as illustrated in FIG. 3A specifically may comprise the substrate 114 comprising the shaft 122 and the contact portion 124, as in a real sensor 110. The shaft 122 specifically may have a length in the range from 20 mm to 70 mm, preferably 50 mm. On one end 152 opposing the contact portion 124 the substrate 114 may comprise a further contact portion 154. The further contact portion 154 may comprise counter contact pads 156. The counter contact pads 156 may be connected to the contacts pads 118. Further, the counter contact pads 156 may be strip-shaped. However, other embodiments are feasible.

For measuring the electrical resistance, the electrical setup according to the first circuit diagram 146 as depicted in FIG. 3B may be applied. The contact pads 118 as depicted in FIG. 3A may be connected to an ohmmeter 158. In this embodiment, all contact pads 118, as illustrated in FIG. 3A, may be connected in series.

For measuring the vibration resistance of the contact pads 118, the electrical setup according to the second circuit diagram 148 as depicted in FIG. 3B may be applied. The second circuit diagram 148 specifically may comprise at least one voltmeter 160, at least one electrical resistor 162 and at least one voltage source 164.

For measuring the insulation resistance, the electrical setup according to the third circuit diagram 150 as depicted in FIG. 3D may be applied. The third circuit diagram 150 specifically may comprise at least one micro-ammeter 166, an electrical resistor 162 and the voltage source 164.

The shaft 122 of the substrate 114 had an average length of around 50 mm. Two test elements 144 were placed opposing each other, particularly the contact pads 118 of the two test elements 144 were placed opposing each other. A maximal discrepancy of ±0.2 mm was tolerated. The two test elements 144 were mechanically secured by applying adhesive strips onto the shaft 122, particularly in a distance of 3 mm to 5 mm to the contact portion 124. Specifically, the two test elements 144 were mechanically secured on a plate. The plate was made of polycarbonate and had a thickness of 2 mm and dimensions from 5 mm×5 mm.

As ohmmeter 158 a Fluke 117 multimeter was applied. As voltmeter 160 an oscilloscope TDS3034 from Tektronix, Beaverton, Oreg., USA was applied. As micro-ammeter, a Keithley 2400 Sourcemeter, Kethley Instruments Inc., Cleveland, Ohio, USA was applied.

For testing the functionality of the sealing ring 134, a simulation testing setup was used, which is schematically shown in FIGS. 4A to 4C. Therein, in FIG. 4A, the testing setup is denoted by reference number 168. For the testing purposes, two test elements 144 as depicted e.g. in FIG. 3A were used, and their contacts portions 124 were pressed together. In FIGS. 4B and 4C, enlarged cross-sectional views of the contact portions 124 are shown, without applying pressure (FIG. 4B) and with applying pressure to the upper one of the two test elements 144 by using a pressure element 232 (FIG. 4C). With this setup, and electrical connection between contact pads 118 of the sensor 110 and electrical contacts of the electronics unit 186 may be simulated. In order to simulate this situation, only the upper one of the two test elements 114 was configured to comprise a sealing ring 134, and, thus, simulates the sensor 110, whereas the lower one of the test elements 114 did not comprise any sealing ring 134 and, thus, simulates the electronics unit 186.

In FIG. 4A the testing setup 168 is depicted. The testing setup 168 comprises at least one terminal block 170 and at least one clamping screw 172. Between a supporting surface 174 of the terminal block 170 and the clamping screw 172, two plates 176 are located. The plates 176 comprise a first plate 178 in mechanical contact with the clamping screw 172 and a second plate 180 attaching to the first plate 178. The first plate 178, in this setup, is a hard plastic plate, whereas the second plate 180 comprises a deformable material such as an elastomeric material, e.g. a foam, and, thus, acts as a pressure element 232.

The two test elements 144 are located in between the pressure element 232 and the supporting surface 174 and each are electrically contacted in order to perform electrical performance tests, such as by using the electrical setups shown in FIGS. 3B to 3D.

As discussed above in the context of FIG. 3A, the test elements 144 each comprise the substrate 114 and the contact pads 118. The substrates 114 each are covered with the electrically insulating material 133 which, thus, forms part of the substrate 114. In the upper test element 144 in FIGS. 4B and 4C, the sealing ring 134 is positioned on top of the electrically insulating material 133.

As shown in FIG. 4B, representing the state without applying pressure by using the clamping screw 172, the sealing ring 134 comprises the sealing lip 138 which, as the first portion of the sealing ring 134, contacts the lower test element 144. As shown in FIG. 4C, once a force 184 is applied by using the clamping screw 172, the pressure element 232 exerts a pressure onto the upper test element 144. The sealing ring 134 is compressed, and the region in the center of the sealing ring 134 is fully or partially bent downward, towards the lower test element 144. As a consequence, the contact pads 118 of the upper test element 144 are pressed onto the corresponding contact pads 118 of the lower test element 144 and an electrical connection is formed, which can be tested with one or more of the setups shown in FIGS. 3B to 3D.

In order to test the functionality of the pressure element 232, the measurement may also be conducted by applying only the first plate 178, leaving out the deformable second plate 180. Similarly, in order to test the functionality of the sealing ring 134, experiments in which none or both of the test elements 144 may comprise the sealing ring 134. Further, the first plate 178 may be removed from the testing setup 168 and pressure may be applied via a finger of a user. Thereby, the performance of the sealing ring 134 and/or of the pressure element 232 may be tested in various ways.

In an experiment, two contact portions 124 of the two test elements 144 were placed on top of each other without the sealing ring 134. A first plate 176 was placed on top of the two test elements 144. Only when the applied force 184 was at least 20 N an electrical contact between the two test elements 144 was observed.

In a further experiment, the first plate was removed and pressure was applied via the finger onto the contact portions 124 of the two test elements 144. An electrical resistance of <1.1 Ohm was observed starting from an estimated value of 1 N to 2 N.

In a further experiment, the second plate 180 was made of Geniomer® 345 from Wacker Chemie AG, Munich, Germany and the second plate 180 had dimensions of 6 mm×6 mm×1 mm. The first plate 180 was made of polycarbonate, had dimensions of 5 mm×5 mm×2 mm and was placed on top of the second plate 180. An electrical resistance of <1.1 Ohm was observed starting from an estimated value of 2.2 N.

In a further experiment, the test elements 144 comprised sealing rings 134. Herein, the previous experiment was repeated. The second plate 180 was made of Geniomer® 345 from Wacker Chemie AG, Munich, Germany and the second plate 180 had dimensions of 6 mm×6 mm×1 mm. The first plate 180 was made of polycarbonate, had dimensions of 5 mm×5 mm×2 mm and was placed on top of the second plate 180. An electrical resistance of <1.1 Ohm was observed starting from an estimated value of 4 N to 5 N.

In a further experiment, the testing setup 168 as described above was applied. The second plate 180 was made of Geniomer® 345 from Wacker Chemie AG, Munich, Germany and the second plate 180 had dimensions of 6 mm×6 mm×1 mm. The first plate 180 was made of polycarbonate, had dimensions of 5 mm×5 mm×2 mm and was placed on top of the second plate 180. A force of around 8 N was applied via the clamping screw 172. The electrical setup according to the second circuit diagram 148 for measuring a vibration resistance as depicted in FIG. 3C and as described above was applied. It was observed, that an electrical connection existed between all contact pads 118. Further, vibrations of 50 Hz with an amplitude of around 1 mm were applied via a solenoid core. No interruptions of the electrical connection between the contact pads 118 was observed.

Further, the electrical setup according to the third circuit diagram 150 for measuring an insulation resistance as depicted in FIG. 3D was utilized and the testing setup 168 as depicted in FIG. 4A was applied. A voltage of 10 V was applied and a current was measured between two single contact pads 118 respectively. A maximal resolution of 0.00001 µA was reached. As a principle uncertainty of plus or minus one digit existed, it may be assumed, that the current had a maximal value of 0.00002 µA. A value for the isolation resistance between two contact pads 118 was determined to 1 Tera-Ohm. The experiment was continued for 21 days at room temperature and the isolation resistance was measured continuously. Thereby, a test solution of PBS buffer and 0.024% of sodium dodecyl sulfate was applied, so that the first plate 178, the second plate 180 and the two test elements 144 were floated with the test solution at 30 mm water column. Comparing to the initial state, no changes were observed. To make sure, that the high isolation resistance was not attributed to an error with the electrical traces 120, the contact pads 118 were released within the test solution and the sealing was lifted. At the moment of lifting the sealing, a maximal current was observed. Therefore, it was demonstrated, that the sealing ring 134 is able to conserve the isolation resistance of 1 Tera-Ohm over a period of a least 21 days.

FIG. 5A and FIG. 5B show an electronics unit 186 of a sensor assembly 256 (shown below in FIGS. 9A to 10B). The electronics unit 186 may form part of a control part 254 of the sensor assembly 256 and may interact with a body mount 212, which will be shown below in FIGS. 6A to 6C. FIG. 5A shows a cross-sectional view of the electronics unit 186, and FIG. 5B shows a bottom view thereof.

The electronics unit 186 may comprise an essentially flat base 188 and a housing 200 covering the base 188 on an upper side 202 opposing a body mount, which will further be described below in more detail. The housing 200 preferably may be a watertight housing 204 having an essentially round shape. The base 188 may protrude from the housing 200 on at least one side, thereby forming a protruding rim 206 on at least one side of the electronics unit 186. The protruding rim 206 may protrude on one side only or may fully or partially surround the electronics unit 186 and, as will be explained in further detail below, may be used for mounting the electronics unit 186 to a body mount 212, as will be further described below. Specifically, the protruding rim 206 may form part of a guiding structure for mounting the electronics unit 186 to the body mount 212 and, thus, may also be referred to as a "second guiding structure" 211, and interacting with a first guiding structure 230 of the body mount 212, as will be further discussed below in the context of FIGS. 9A to 10B.

The housing 200 may fully or at least partially cover the electronics unit 186 and may provide protection against mechanical influences and moisture. Specifically, the electronics unit 186 may comprise one or more electronics components 208, which are fully or partially covered by the housing 200.

The electronics unit 186, such as by using one or more of the electronics components 208, specifically may be configured for one or more of controlling the detection of the analyte or transmitting measurement data to another component, such as a receiver outside the sensor assembly. Therein, a wireless or a wire bound transmission may take place.

The electronics unit 186, for contacting the sensor 110 as will be explained in further detail below, may comprise at least two electrical contacts 210. The electrical contacts 210 may be electrically connected to the contact pads 118 of the sensor 110, as described above and as described in further detail below in the context of e.g. FIGS. 9A to 10B, once the electronics unit 186 is mounted to the body mount 212. The electrical contacts 210 may be located on a lower side 209 of base 188 and may be electrically connected to one or more of the electronics components 208 inside the housing 200 by vias 213. Thus, as an example, the base 188 may be or may comprise one or more circuit boards, such as one or more printed circuit boards, such as one or more rigid printed circuit boards, and the vias 213 may penetrate the printed circuit board from the lower side 209, facing the body mount 212, to the upper side 202, facing the interior of the housing 200. The one or more electronics components 208 may be applied to the printed circuit board on the upper side 202. Further, one or more electrical leads or traces may be applied to the printed circuit board. It shall be noted, however, that other setups of the electronics unit 186 are feasible.

FIGS. 6A to 6C show an exemplary embodiment of a body mount 212 of the sensor assembly 256 in a cross-sectional view (FIG. 6A) as well as in partial perspective views of components of the body mount 212 (FIGS. 6B and 6C).

The body mount 212 may be configured for attachment to a body of a user. The body mount 212 may comprise a base 234 as depicted in FIG. 6B in a perspective view, and a lever 218 as depicted in FIG. 6C in a perspective view. The sensor assembly 256 will further be discussed below in more detail in the context of FIGS. 9A to 10B.

The body mount 212 may comprise at least one mounting element 217 for mounting the body mount 212 to the skin of the user. In the exemplary embodiment shown in FIGS. 6A and 6B, the mounting element 217 may comprise at least one plaster 215 having an adhesive surface 214 which may be adhered to the skin of the user. The plaster 215 may have an arbitrary shape, for example a rectangular shape or an oval shape. However, other embodiments are feasible. The adhesive surface 214 may be provided with a protective liner (not shown) which may be removed before adhering the adhesive surface 214 to the skin of the user.

Further, the body mount 212 may comprise a receptacle 228 on a side opposing the lever 218. The receptacle 228 may be capable of receiving a part of the electronics unit 186. As an example, the receptacle 228 may receive the protruding rim 206 of 188 of the electronics unit 186 or a to part thereof, which, as outlined above, may act as a second guiding structure 211, as explained above in the context of FIGS. 5B and 5B. The body mount 212 may comprise a first guiding structure 230, and the receptacle 228 may form part of this first guiding structure 230.

Further, the body mount 212, particularly the base 234, may include a locking mechanism 216 having at least one lever 218 pivotably mounted to the body mount 212. Specifically, the lever 218 may be attached to one end 220 of the body mount 212, such as to one end of the base 234. The lever 218 may be permanently or removably mounted to the body mount 212. The lever 218, as an example, may be or may comprise a knee lever 222. A flexible extension 224, specifically a foldable foil 226, may be fixed to an outer end of the lever 218, capable of being gripped by a user for opening the lever 222.

The locking mechanism 216 specifically may be a self-locking mechanism 219. As explained in further detail above, the self-locking may be induced in such a way that, when the electronics unit 186 is inserted into the body mount 212, the electronics unit 186 exerts a force onto the lever 218 which holds the lever in a closed state or closed position. Thus, as will be explained in the context of FIG. 10B below, the locking mechanism 216 may have an open state or open position, such as when the lever 218 is opened or pivoted in a vertical position, in which the electronics unit 186 may be taken out of the body mount 212. When the electronics unit 186 is inserted into the body mount 212, the lever 218 may be pivoted in a horizontal position, as will be shown in the context of FIG. 10A below, in which the locking mechanism 216 is in a closed state or closed position. In this closed state or closed position, the electronics unit 186 may exert a force onto the lever 218 which holds the lever 218 in the closed position.

For this purpose, the lever 218, as depicted in FIG. 6C, may be shaped in a specific way. The lever 218 is connected to the base 234 of the body mount 212 by a hinge 221, comprising e.g. sleeves 223 on the body mount 212 and corresponding studs 225 on the lever 218, such that the lever 218 may be pivoted. The lever 218 specifically may be designed as a knee-lever 222, having a protrusion 227 which faces inwardly. The protrusion, in conjunction with a main lever arm 229 of the lever 218, may form a further receptacle 231, into which, as depicted in FIG. 10B below, the rim 206 or a part thereof of base 188 may be inserted. The receptacle 231 may also form part of the first guiding structure 230 of the body mount 212.

The first guiding structure 230 and the second guiding structure 211 of the electronics unit 186 as illustrated within FIGS. 5B and 5B may be configured to interact such that the electronics unit 186 may be positioned relative to the body mount 212 in a state in which the electronics unit 186 is locked to the body mount 212.

Further, a pressure element 232 may be integrated into the base 234 of the body mount 212, such as by adhering the pressure element 232 to the base 234 and/or by integrating the 234 with the pressure element 232 by multicomponent injection molding. The pressure element 232 may be integrated into a cavity 233 of the base 234 as depicted in FIG. 6B. The pressure element 232 may be one or both of flexible or deformable. Particularly, the pressure element 232 may comprise at least one of: an elastomer; a foam; a textile; a spring element; a thermoplastic polymer. Exemplarily, the pressure element 232 may be made of Geniomer® 345 from Wacker Chemie AG, Munich, Germany. The pressure element 232 may have an arbitrary shape. For example, the pressure element 232 may have a cylindrical shape. However, other embodiments are feasible. The body mount 212 may further comprise at least one opening 235 which fully penetrates the body mount 212, specifically the base 234 and the adhesive surface 214. The opening 235 may be located next to the pressure element 232. The opening 235 may exemplarily have a round or a rectangular cross-section. However, other embodiments are feasible. As explained in further detail below, such as in the context of FIG. 8B, 8C, 8D, 9A or 10B, the opening 235 may be used for guiding the cannula 242 and/or the sensor 110 into the body tissue and, thus, the cannula 242 and/or the shaft 122 of the sensor 110 may pass through the opening 235.

FIGS. 7A to 7C show different embodiments of an insertion element 236. The insertion element 236 may be configured for transferring the sensor 110 as described above to the body mount 212. The insertion element 236 may comprise at least one plunger 238. Further, the insertion element 236 may comprise at least one cannula 242, specifically at least one slotted cannula 244. Thus, the transfer of the sensor 110 to the body mount 212, by using the insertion element 236, may take place simultaneously to an insertion of the shaft 122 of the sensor 110 or a part thereof into the body tissue, even though these processes actually are separate processes and may also be performed independently. Thus, as an example, the insertion element 236 may be designed without the cannula 242, and may be used for connecting the sensor 110 to the body mount 212, only. For implanting or inserting the sensor 110 into the body tissue, a separate tool may be used in this case.

The sensor 110 may be partially, specifically with at least one insertable portion 246, received in the cannula 242. Specifically, the contact portion 124 may be located outside the cannula 242 and the insertable portion 146 may comprise the shaft 122 of the sensor 110 or may be part of the shaft 122.

For adhering the sensor 110 to the body mount 212, one or more first adhesive elements 248 may be used. The at least one first adhesive element 248 may be attached to one or both of the body mount 212 and/or to the sensor 110. The first adhesive element 248, as an example, may comprise at least one adhesive, such as at least one pressure sensitive adhesive, like a polymer adhesive or a silicone-based adhesive. Other examples are feasible. Further, the first adhesive element 248 may also fully or partially be integrated or attached to the pressure element 232. The first adhesive element 248 may be designed to keep the sensor 110 in place, fixedly mounted to the body mount 212, once the sensor 110 is transferred onto the body mount 212 by using the insertion element 236.

Further, for preliminarily attaching the sensor 110 to the insertion element 236, such as to the plunger 238, at least one second adhesive element 250 may be used. The second adhesive element 250 may be attached to and/or integrated into one or both of the sensor 110 and/or the insertion element 236, such as the plunger 238. Specifically, however, the second adhesive element 250 may be attached to or part of the sensor 110. This embodiment specifically may be realized by using the sealing ring 134, which may have adhesive properties, as the second adhesive element 250. Thus, during transfer of the sensor 110 to the body mount 212, the sealing ring 134 may stick to the plunger 238 and, thus, may attach the sensor 110 to a bottom side 252 of the plunger 238.

As can be seen in the figures, the first and second adhesive elements 248, 250 may contact the sensor 110, specifically the contact portion 124 of the sensor 110, on opposite sides thereof. The insertion element 236 may be configured such that the sensor 110 may be inserted into the skin of the user in a direction transverse to a direction of extension of the skin, particularly perpendicular to the direction of extension (FIG. 7B) or in an angle in the range from 20° to 70°, preferably from 30° to 50° (FIGS. 7A and 7C). Other embodiments are feasible.

FIGS. 8A to 8D illustrate a method of mounting the sensor 110 to the body mount 212 attachable to the skin of the user. In a first step, as depicted in FIG. 8A, the body mount 212 may be provided, having the base 234 and the pressure element 232 disposed thereon or integrated therein and with the opening 235 penetrating the base 234. The first adhesive element 248 may be attached to or be part of the pressure element 232. Specifically, this may be realized by using the pressure element 232, which may have adhesive properties, as the first adhesive element 248. The body mount 212, in this state, may be attached to the skin of the user by using the mounting element 217, such as the plaster 215, as disclosed above. The body mount 212 may further comprise the locking mechanism 216 as explained above and as will be disclosed in further detail below.

In a next step, as depicted in FIG. 8B, the sensor 110 and the insertion element 236 as illustrated in FIGS. 7A to 7C may be provided. In a next step, as depicted in FIG. 8C, the sensor 110 may be transferred from an initial position, in which the sensor 110 is attached to the insertion element 236, as depicted in FIG. 8B, into a final position in which the sensor 110 is attached to the body mount 212 via the first adhesive element 248 and released from the insertion element 236, by using the insertion element 236. Thus, during the transfer, the adhesion between the sensor 110 and the body mount 212 may be established by the first adhesive element 248 and the adhesion between the sensor 110 and the insertion element 236, established by the second adhesive element 250, is released. Thereafter, the insertion element 236 may be removed.

In a next step, as depicted in FIG. 8D, the electronics unit 186 may be locked onto the body mount 212 by using the at least one locking mechanism 216 as illustrated in FIGS. 6A to 6C. The electronics unit 186 and the body mount 212 may form a control part 254 of a sensor assembly 256.

FIGS. 9A and 9B show an exemplary embodiment of the sensor assembly 256 in a cross-sectional view (FIG. 9A) and in a side view (FIG. 9B). The sensor assembly 256 may comprise the control part 254 having the body mount 212 and the electronics unit 186. For further details, reference can be made to the description of FIGS. 1A to 8D above.

FIGS. 10A and 10B show a further exemplary embodiment of the sensor assembly 256 in a perspective view in a fully assembled state, in which the locking mechanism 216 is locked and in a closed state or closed position (FIG. 10A) and in a disassembled state, in which the locking mechanism 216 is unlocked and in an opened state or opened position (FIG. 10B). As explained above in the context of FIGS. 6A to 6C, this locking or unlocking specifically may be performed by pivoting the lever arm 229 of lever 218.

The sensor assembly 256 may comprise the control part 254 comprising the body mount 212 and the electronics unit 186. Whereas the sensor assembly 256 according to FIGS. 9A and 9B may comprise the electronics unit 186 with an essentially round shape, the sensor assembly 256 may comprise the electronics unit 186 with an essentially flat shape. Thus, however, is simply a design matter, and other embodiments may be feasible. For further details, reference can be made to the descriptions of the FIGS. 1A to 8D.

By mounting the electronics unit 186 onto the body mount 212, the electrical contacts 210 of the electronics unit 186, disposed on the lower side 209 of the electronics unit 186, which in shape and position correspond to the contact pads 118 of the sensor 110, may be pressed onto the contact pads 118 or vice a versa, such that a mutual electrical contact between corresponding contact pads 118 and the electrical contacts 210 may be established. Simultaneously, as symbolically shown in the test setup of FIG. 4C, the sealing ring 134 may be compressed, and a contact region may be isolated from the ambient atmosphere by the sealing ring 134. The pressure element 232 may establish the required deformation of the substrate 114 of the sensor 110 and may provide, in conjunction with the locking mechanism 216, the required pressure for establishing a durable and reliable electrical contact between the sensor 110 and the electronics unit 186.

LIST OF REFERENCE NUMBERS 110 sensor
112 intermediate product
114 substrate
116 electrode
118 contact pad
120 electrical trace
122 shaft
124 contact portion
125 surface
126 contact surface area
128 working electrode
130 counter electrode
132 reference electrode
133 electrically insulating material
134 sealing ring
135 insulating surface area
136 insulating layer
138 sealing lip
140 inner perimeter
142 outer perimeter
144 test element
146 first circuit diagram
148 second circuit diagram
150 third circuit diagram
152 end
154 further contact portion 156 counter contact pads
158 ohmmeter
160 voltmeter
162 electrical resistor
164 voltage source
166 micro-ammeter
168 testing setup
170 terminal block
172 clamping screw
174 supporting surface
176 plate
178 first plate
180 second plate
184 force
186 electronics unit
188 base
200 housing
202 upper side
204 watertight housing
206 rim
208 electronics component
209 lower side
210 electrical contacts
211 second guiding structure
212 body mount
213 vias
214 adhesive surface
215 plaster
216 locking mechanism
217 mounting element
218 lever
219 self-locking mechanism
220 end
221 hinge
222 knee lever
223 sleeve
224 flexible extension
225 stud
226 foldable foil
227 protusion
228 receptacle
229 lever arm
230 first guiding structure
231 further receptacle
232 pressure element
233 cavity
234 base
235 opening
236 insertion element
238 plunger
242 cannula
244 slotted cannula
246 insertable portion
248 first adhesive element
250 second adhesive element
252 bottom side
254 control part
256 sensor assembly

The invention claimed is:

1. A sensor for detecting at least one analyte in a body fluid, the sensor comprising:
at least one substrate;
at least two electrodes applied to the at least one substrate, the electrodes being adapted for detecting the analyte;
at least two contact pads applied to the at least one substrate;
at least two electrical traces applied to the at least one substrate, the at least two electrical traces electrically connecting the at least two electrodes and the at least two contact pads, the at least two contact pads being commonly located as a group on a surface of the at least one substrate; and
a sealing ring comprising a single ring-shaped element made of at least one compressible material and fixedly applied to the at least one substrate, the sealing ring commonly surrounding the group of the at least two contact pads, the ring-shaped element being configured to be compressed against a surface to provide a seal of the at least two contact pads from the environment.

2. The sensor according to claim 1, wherein the sealing ring comprises at least one material selected from the group consisting of: a polymer; an elastomer; a silicone material; a silicone polymer; a silicone copolymer; an elastomer comprising at least one silicone copolymer; an elastomer comprising at least one polyurea copolymer; an elastomer comprising a copolymer of polydimethylsiloxane; an elastomer comprising a copolymer of dimethylsiloxane and urea; a poly(dimethylsiloxane)-polyurea copolymer; a thermoplastic elastomer; a cured elastomer.

3. The sensor according to claim 1, wherein the sealing ring has a shape selected from the group consisting of: a circular shape, an oval shape, a polygon shape, a rectangular shape.

4. The sensor according to claim 1, wherein the sensor further comprises at least one electrically insulating material, the electrically insulating material at least partially covering the at least two electrical traces, the electrically insulating material leaving open the at least two electrodes and the at least two contact pads, wherein the sealing ring fully or partially is applied onto the electrically insulating material.

5. The sensor according to claim 1, wherein the sealing ring is produced by applying a liquid or pasty sealing material to the at least one substrate, wherein the liquid or pasty sealing material is fully or partially hardened after application.

6. A sensor assembly for detecting at least one analyte in a body fluid, the sensor assembly comprising at least one sensor according to claim 1, the sensor assembly further comprising at least one control part having at least one electronics unit for one or more of controlling the detection of the analyte or transmitting measurement data to another component, wherein the control part comprises at least two electrical contacts electrically connected to the at least two contact pads of the sensor, the sealing ring being configured to be compressed between the substrate and the control part to seal the at least two electrical contacts and the at least two contact pads within the interior of the sealing ring from the environment.

7. The sensor assembly according to claim 6, wherein the sensor assembly further comprises at least one pressure element configured for pressing the at least two contact pads of the sensor onto the at least two electrical contacts of the control part or vice versa.

8. The sensor assembly according to claim 7, wherein the pressure element is one or both of flexible or deformable.

9. The sensor assembly of claim 6 in which the sealing ring extends outwardly from the substrate a distance to form a ring of sealing material surrounding the at least two contact pads.

10. The sensor assembly of claim 6 in which the sealing ring is configured to be compressed against a surface of the electronics unit with the at least two electrical contacts of the electronics unit electrically connected to the at least two contact pads of the sensor.

11. The sensor of claim 1 in which the sealing ring extends outwardly from the substrate a distance to form a ring of sealing material surrounding the at least two contact pads.

12. The sensor of claim 1 in which the sealing ring extends outwardly from the substrate a distance to exceed the contact pads.

13. The sensor of claim 12 in which the sealing lip is configured such that the sealing lip is the first part of the sealing ring to contact a surface when the sealing ring is pressed onto the surface.

14. The sensor of claim 1 in which the sealing ring includes a sealing lip.

15. The sensor of claim 1 in which the sealing ring is configured to be compressed against a surface of an electronics unit when the sensor is positioned for use with the electronics unit with the at least two contact pads electrically connected with electrical contacts of the electronics unit.

16. The sensor of claim 1 in which each of the at least two contact pads is received within the ring-shaped sealing element.

17. A sensor for detecting at least one analyte in a body fluid, the sensor comprising:
a substrate;
at least two electrodes applied to the substrate, the electrodes being adapted for detecting the analyte;
at least two contact pads applied to the substrate;
at least two electrical traces applied to the substrate, the at least two electrical traces electrically connecting the at least two electrodes and the at least two contact pads, the at least two contact pads being located together on a surface of the substrate; and
a single ring-shaped element applied to the substrate and configured to surround the at least two contact pads within a single enclosure, the ring-shaped element extending outwardly from the substrate farther than the contact pads, the ring-shaped element being configured to be pressed against a surface to provide a seal of the at least two contact pads from the environment.

* * * * *